(12) United States Patent
Watt et al.

(10) Patent No.: US 10,449,186 B2
(45) Date of Patent: Oct. 22, 2019

(54) PHENYLETHYNYL-SUBSTITUTED BENZENES AND HETEROCYCLES FOR THE TREATMENT OF CANCER

(71) Applicant: UNIVERSITY OF KENTUCKY RESEARCH FOUNDATION, Lexington, KY (US)

(72) Inventors: David S. Watt, Lexington, KY (US); Chunming Liu, Lexington, KY (US); Vitaliy M. Sviripa, Lexington, KY (US); Wen Zhang, Lexington, KY (US); Markos Leggas, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/976,643

(22) Filed: May 10, 2018

(65) Prior Publication Data

US 2018/0369222 A1    Dec. 27, 2018

Related U.S. Application Data

(60) Provisional application No. 62/636,463, filed on Feb. 28, 2018, provisional application No. 62/523,081, filed on Jun. 21, 2017.

(51) Int. Cl.

| | |
|---|---|
| *A61P 35/00* | (2006.01) |
| *A61K 31/45* | (2006.01) |
| *A61K 31/495* | (2006.01) |
| *A61K 31/40* | (2006.01) |
| *A61K 31/4418* | (2006.01) |
| *A61K 31/4439* | (2006.01) |
| *A61K 31/4965* | (2006.01) |
| *A61K 31/404* | (2006.01) |
| *A61K 31/416* | (2006.01) |
| *A61K 31/437* | (2006.01) |
| *A61K 31/47* | (2006.01) |
| *A61K 31/4706* | (2006.01) |
| *A61K 31/472* | (2006.01) |
| *A61K 31/4725* | (2006.01) |
| *A61K 31/5375* | (2006.01) |

(52) U.S. Cl.
CPC ............. *A61K 31/45* (2013.01); *A61K 31/40* (2013.01); *A61K 31/404* (2013.01); *A61K 31/416* (2013.01); *A61K 31/437* (2013.01); *A61K 31/4418* (2013.01); *A61K 31/4439* (2013.01); *A61K 31/47* (2013.01); *A61K 31/472* (2013.01); *A61K 31/4706* (2013.01); *A61K 31/4725* (2013.01); *A61K 31/495* (2013.01); *A61K 31/4965* (2013.01); *A61K 31/5375* (2013.01); *A61P 35/00* (2018.01)

(58) Field of Classification Search
CPC ...................................................... A61P 35/00
See application file for complete search history.

(56) References Cited

FOREIGN PATENT DOCUMENTS

| | | | |
|---|---|---|---|
| WO | WO-9902497 A2 * | 1/1999 | ........... C07D 213/00 |
| WO | 03/037333 A1 | 5/2003 | |
| WO | WO-2005094822 A1 * | 10/2005 | ........... C07D 213/16 |

\* cited by examiner

*Primary Examiner* — Theodore R. West
(74) *Attorney, Agent, or Firm* — Stites & Harbison PLLC; Sean P. Ritchie (57) ABSTRACT

Halogenated phenylethynyl-substituted heterocycles that possess either an N-alkylamino or N,N-dialkylamino group attached to the heterocycle or halogenated phenylethynyl-substituted benzenes that a nitrogen-containing heterocycle attached to the benzene inhibit the proliferation cancer cells and are useful antineoplastic agents.

20 Claims, 2 Drawing Sheets

PHENYLETHYNYL-SUBSTITUTED BENZENES AND HETEROCYCLES FOR THE TREATMENT OF CANCER

CROSS-REFERENCE TO RELATED APPLICATIONS

This application claims the benefit of U.S. Provisional Application No. 62/523,081 filed 21 Jun. 2017 and the benefit of U.S. Provisional Application No. 62/636,463 filed 28 Feb. 2018, the entire disclosures of each of which are hereby incorporated by reference herein.

STATEMENT REGARDING FEDERALLY SPONSORED RESEARCH

This work was supported by NIH grant numbers R01 CA172379 and P30 GM110787 and was also supported by the Office of the Assistant Secretary of Defense for Health Affairs, through the Prostate Cancer Research Program under Award No. W81XWH-16-1-0635. The government has certain rights in the subject technology.

TECHNICAL FIELD

The present disclosure relates to compounds that treat cancer and/or treat or prevent cancer metastasis. In particular, the subject technology is directed to halogenated phenylethynyl-substituted benzenes bearing nitrogen-containing heterocycles attached to the benzene and directed to halogenated phenylethynyl-substituted nitrogen-containing heterocycles, their salts and their pharmaceutical compositions and methods for treating cancer therewith.

BACKGROUND

A family of fluorinated N,N-dialkylaminostilbene analogs that inhibit the expression of Wnt target genes, such as c-myc, and repress colon cancer cell growth in vitro and in vivo was reported. See, e.g., *J Med Chem* 2011, 54:1288-1297; *ACS Chem Biol* 2013, 8(4):796-803; *J Med Chem* 2014, 57:6083-91; U.S. Pat. No. 8,664,276.

In addition, certain diarylacetylenes are known for certain medicinal uses. See, e.g., WO2012149049; WO2012149048; WO2010092043; WO2009038759; WO2008073350; and WO2001029011. Further, U.S. Pat. No. 8,716,355 to Tsai discloses hydroxylated tolans and related compounds in the treatment of cancer and Hadfield et al. disclose preparation and evaluation of diarylalkynes as antitumor agents. Hadfield et al., *Synth Commun.* 1998, 28(8):1421-1431.

Halogenated diarylacetylenes and methods for treating cancer have also been reported. See U.S. patent application publication number 2015-0272908; Sviripa, et al. "Halogenated diarylacetylenes repress c-myc expression in cancer cells", *Bioorg Med Chem Lett* 2014, 24:3638-40.

However, there is an ongoing need for additional compounds that can be used to treat cancer and other ailments.

SUMMARY OF THE DISCLOSURE

Advantages of the present disclosure include halogenated phenylethynyl-substituted benzenes or heterocycles and pharmaceutical compositions thereof which have antineoplastic activity and methods of inhibiting cancer cell growth and/or treating cancer in a patient by administering one or more of the halogenated phenylethynyl-substituted heterocycles or pharmaceutical compositions thereof.

One aspect of the present disclosure is directed to halogenated phenylethynyl-substituted benzenes or heterocycles that are useful for killing hyperproliferating cells such as cancer cells for the treatment of human malignant and benign cancers, including without limitation, colorectal cancer (CRC), leukemias, breast cancer, ovarian cancer, lung cancer, prostate cancer, and liver cancer. In this aspect of the disclosure, there are provided certain halogenated phenylethynyl-substituted heterocycles having anti-neoplastic activity against cancerous cells. The halogenated phenylethynyl-substituted benzenes and heterocycles of the present disclosure include compounds according to formulas (I), (II) and (III):

or a pharmaceutically acceptable salt thereof, wherein each of $X_1$ through $X_5$ independently represents H, lower alkyl, alkoxy, e.g., lower alkoxy, halo, and/or $NR_1R_2$, wherein each of $R_1$ and $R_2$ independently represents H, or a lower alkyl, n is either 1 or 0 and when n is 1, each of $Y_1$ through $Y_4$ independently represents H, a lower alkyl or alkoxy, or $NR_1R_2$. Heterocycle represents a heterocycle ring that can be unsubstituted or substituted with one or more lower alkyl or alkoxy, e.g., lower alkoxy groups, and/or one or more halogens; wherein the heterocycle is selected among oxopiperidine, morpholine, piperazine, N-methylpiperazine, N-pyrrole, and 2,5-dimethyl-N-pyrrole, quinoline, isoquinoline, indole, indazole, naphthyridine, and pyridinyl; and $Y_5$ represents one or more $NR_1R_2$, and/or one or more halogens which can be the same or different.

The halogenated phenylethynyl-substituted benzenes or heterocycles of formulas (I), (II), or (III) or pharmaceutically acceptable salts thereof can be included in a pharmaceutical composition with a pharmaceutically acceptable carrier.

Another aspect of the present disclosure is directed to methods of treating cancer, e.g., inhibiting cancer cell growth and/or inhibiting tumor growth in a mammal, such as a human, or treating diseases associated with hyperproliferating cells. In one embodiment of this aspect of the disclosure, an effective amount of one or more halogenated phenylethynyl-substituted benzenes or heterocycles, pharmaceutical salts and/or pharmaceutical compositions thereof is administered to a patient in need of treatment of cancer sufficient to treat/inhibit cancer cell growth in the patient.

In an embodiment of this aspect of the disclosure, a therapeutically effective amount of one or more halogenated phenylethynyl-substituted benzenes and heterocycles, pharmaceutical salts and/or pharmaceutical compositions thereof is administered to a patient suffering from colorectal cancer. In another embodiment, a therapeutically effective amount of one or more halogenated phenylethynyl-substituted benzenes bearing nitrogen-containing heterocycles attached to the benzene and one or more halogenated nitrogen-containing phenylethynyl-substituted heterocycles, pharmaceutical salts and/or pharmaceutical compositions thereof is administered to a patient suffering from liver cancer or prostate cancer.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIG. 1 shows the structural formula for 2,6-difluoro-4'-(N,N-dimethylamino)stilbene (1) and 2,6-difluorophenyl-4'-(N,N-dimethylamino)phenylacetylene (2). FIG. 1 also illustrates a synthesis for heterocyclic-substituted phenylethynyl benzenes 4 and phenylethynyl-substituted heterocycles 5 and 7. Legend: a, heterocyclic-substituted phenyl iodide, iPr$_2$EtN, Pd(PPh$_3$)$_4$, CuI, H$_2$O, 80° C.; b, heteroaryl iodide, iPr$_2$EtN, Pd(PPh$_3$)$_4$, CuI, H$_2$O, 80° C.; c, chloro-substituted heteroaryl iodide, iPr$_2$EtN, Pd(PPh$_3$)$_4$, CuI, H$_2$O, 75° C. followed by mono- or dialkylamine, THF, 130° C., 2-3 h, pressure tube; d, fluorinated heteroaryl iodide, iPr$_2$EtN, Pd(PPh$_3$)$_4$, CuI, H$_2$O, 80° C.

DETAILED DESCRIPTION OF THE DISCLOSURE

The present disclosure relates to halogenated phenylethynyl-substituted benzenes and heterocycles, their salts and their pharmaceutical compositions and methods of inhibiting cancer cell growth and/or treating cancer in a patient by administering one or more of the halogenated phenylethynyl-substituted benzenes and heterocycles, a pharmaceutical salt thereof, or a pharmaceutical composition thereof. It was found that halogenated phenylethynyl-substituted benzenes and heterocycles having at least one, preferably two, halo substituents in one aryl ring and an amine in the opposing aryl or heteroaryl ring, e.g., N-methylamino or N,N-dimethylamino, inhibit the proliferation of LS174T colon cancer cells through the inhibition of c-myc and induction of the cyclin-dependent kinase inhibitor-1 (i.e., p21$^{Wif1/Cip1}$). Such compounds and compositions are useful as antineoplastic agents.

The halogenated phenylethynyl-substituted benzenes and heterocycles of the present disclosure include at least one amine group, e.g., a primary, secondary or tertiary amine, on the benzene or in the heterocycle ring of the halogenated phenylethynyl-substituted benzenes and heterocycles. Such compounds are useful as antineoplastic agents and can be represented by the following formula:

(I)

or a pharmaceutically acceptable salt thereof. The substituents of $X_1$ through $X_5$ each independently represent H, a lower alkyl or alkoxy, e.g., lower alkoxy, halo, and/or NR$_1$R$_2$, wherein each of R$_1$ and R$_2$ independently represents H, or a lower alkyl. In an embodiment of the present disclosure at least one of $X_1$ through $X_5$ is a halo and the remaining $X_1$ through $X_5$ represent H, a lower alkyl or lower alkoxy. In another embodiment of the present disclosure at least of $X_1$ through $X_5$ is NR$_1$R$_2$. A halo group means an F, Cl, Br, or I. Preferably substituents $X_1$ through $X_5$ include at least two halo groups, e.g., F and/or Cl. In an embodiment of the present disclosure, $X_1$ and $X_5$ are halo groups such as two F groups, two Cl groups or an F and Cl group.

The variable n can be 1 or 0. When n is 1, the halogenated phenylethynyl-substituted benzenes of formula (I) can be represented by formula (II) below.

(II)

For formula (II), each of $Y_1$ through $Y_4$ independently represents H, a lower alkyl, or NR$_1$R$_2$, wherein each of R$_1$ and R$_2$ independently represents H, or a lower alkyl.

When n is 0, formula (I) can be represented by the halogenated phenylethynyl-substituted heterocycles of formula (III) below.

The substituents of $X_1$ through $X_5$ for formula (II) and (III) are as described for formula (I) including all combinations thereof. For each of formulas (I), (II) and (III), Heterocycle represents a heterocyclic ring. For example, Heterocycle represents a heterocycle ring that can be selected from among oxopiperidine, morpholine, piperazine, N-methylpiperazine, N-pyrrole, and 2,5-dimethyl-N-pyrrole, quinoline, isoquinoline, indole, indazole, naphthyridine and pyridinyl. For each of formulas (I), (II) and (III), the heterocycle ring can be unsubstituted or substituted with one or more lower alkyl or alkoxy, e.g., lower alkoxy groups, and/or one or more halogens. The variable $Y_5$ in each of formulas (I), (II), and (III) represents one or more $NR_1R_2$, and/or one or more halogens which can be the same or different, that is each $NR_1R_2$ group can have the same or different $R_1$ and $R_2$, wherein each of $R_1$ and $R_2$ independently represents H, or a lower alkyl, and/or the Heterocycle can have one or more of the same or different halogen. In an embodiment of the present disclosure, $Y_5$ in each formulas (I), (II), and (III) represents one or more $NR_1R_2$. In another embodiment of the present disclosure, $Y_5$ in each of formulas (I), (II), and (III) represents one or more halogens. For example, for formula (III), at least one of $X_1$ through $X_5$ is $NR_1R_2$ and Heterocycle represents a pyridinyl ring having at least one halogen and preferably two halogen groups, e.g. fluoro and/or chloro groups.

The term "lower alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups having from one to about ten carbons ($C_1$-$C_{10}$), e.g., from one to about six carbon atoms ($C_1$-$C_6$) in its backbone structure. In one aspect of the present disclosure, the lower alkyl groups specifically include methyl, ethyl, propyl, isopropyl, n-butyl, etc.

Embodiments of the halogenated phenylethynyl-substituted benzenes and heterocycles of the present disclosure include wherein at least two of $X_1$ through $X_5$ are halo groups, e.g., wherein at least two of $X_1$ through $X_5$ are either (i) a fluoro and chloro, (ii) both fluoro, (iii) both chloro groups, and wherein both $R_1$ and $R_2$ are lower alkyl groups, e.g., methyl, ethyl, or butyl groups. Preferably $X_1$ and/or $X_5$ are halo groups, e.g., the phenylethynyl-substituted benzenes and heterocycles have one or two halogen substituents at ortho-positions relative to the acetylenic linkage, and $X_2$ through $X_4$ are H or a lower alkyl or alkoxy. In some embodiments, the halogenated phenylethynyl-substituted benzenes and heterocycles include compounds, or a pharmaceutically acceptable salt thereof, where $Y_3$ is $NR_1R_2$, and $Y_1$, $Y_2$, $Y_4$, and $Y_5$ independently represent H, a lower alkyl, or $NR_1R_2$. In other embodiments, $Y_3$ is $NR_1R_2$, and $Y_1$, $Y_2$, $Y_4$, and $Y_5$ independently represent H or a lower alkyl, e.g. $Y_1$, $Y_2$, $Y_4$, and $Y_5$ represent H. In still further embodiments, at least one of $R_1$, or $R_2$, is a lower alkyl.

Pharmaceutical compositions of the present disclosure include a pharmaceutically acceptable carrier and one or more of compounds according to formulas (I), (II), or (III), or a pharmaceutically acceptable salt of a compound of formulas (I), (II), or (III).

In one aspect of the present disclosure, the compounds of formula (I), (II) or (III), a pharmaceutically acceptable salt thereof, or a pharmaceutically acceptable composition thereof is used in the treatment of cancer. The method comprises administering to a patient in need of such treatment an effective amount of one or more of the halogenated phenylethynyl-substituted heterocycles, a pharmaceutical salt thereof, or a pharmaceutical composition thereof. Embodiments of the method include wherein the cancer treated is selected from among colorectal cancer, leukemias, breast cancer, ovarian cancer, lung cancer, prostate cancer and liver cancer.

In the course of studies focused on the mechanisms of colorectal cancers, we employed chemical biology to probe cell signaling events that regulate gene expression. Selective targeting of key steps in this process offered the potential for developing therapeutic agents to treat these cancers. We reported, for example, that the 2',6'-dihalostyrylanilines (1) (FIG. 1) inhibited the expression of Wnt target genes, such as c-myc, and repressed colon cancer LS174T cell growth in vitro and in vivo. See, e.g., J Med Chem 2011, 54:1288-1297; ACS Chem Biol 2013, 8(4):796-803; J Med Chem 2014, 57, 6083-91. We established that this agent targeted exclusively the catalytic subunit of the oligomeric enzyme, methionine S-adenosyltranferase-2 (MAT2) that furnishes S-adenosylmethionine (SAM) to regulatory methyltransferases and that is upregulated in a selected group of cancers. We further established that heterocyclic variants of these 2',6'-dihalostyrylanilines (1) possessed minimal gross toxicity, no human ether-à-go-go-related protein (hERG) activation as desired, reasonable bioavailability and pharmacokinetics. As desired, these stilbene-based agents did not affect methionine S-adenosyltransferase-1 (MAT1) that served as the principal source of SAM necessary for other cellular needs. Unlike a recent report of other MAT2A inhibitors, we also demonstrated in vivo potency in a xenograft model using colorectal cancer cells.

Figure 1:
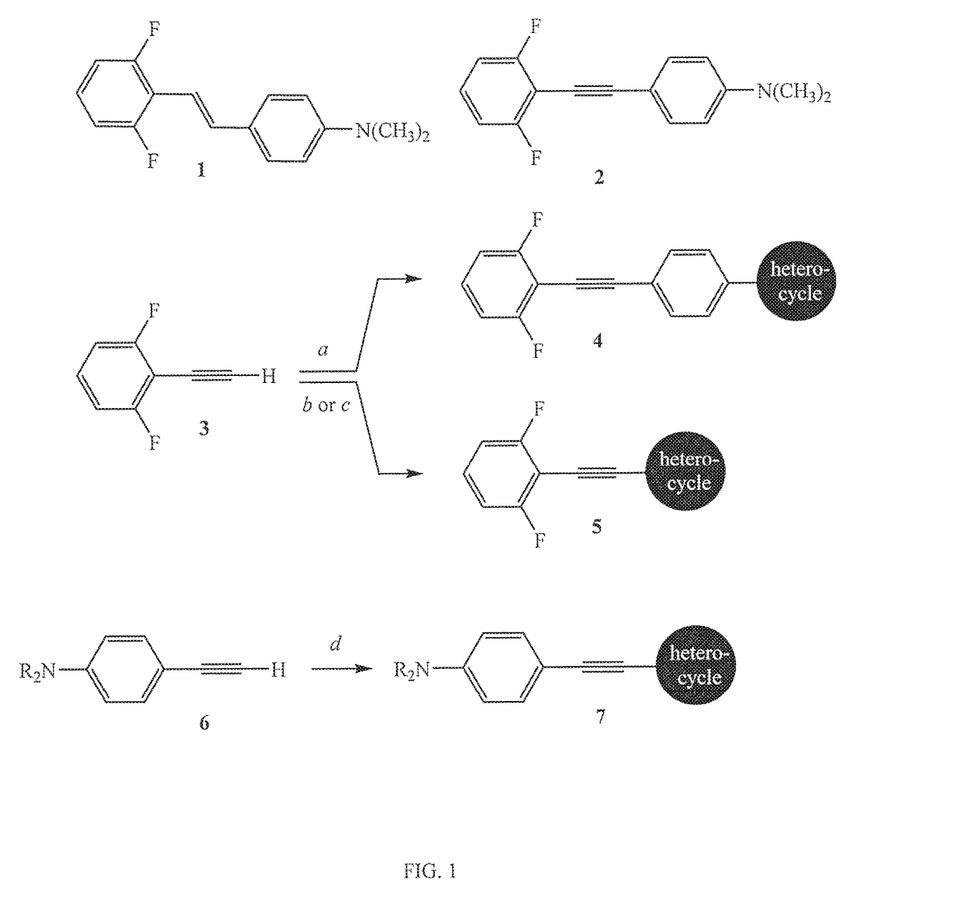

Concerns regarding thermal or photochemical EZ-isomerizations in stilbenes 1 that could potentially complicate future pharmacokinetic and pharmacodynamic studies led to synthesis and evaluation of the analogous diarylacetylenes 2 (FIG. 1). In accord with the SAR study of the stilbenes 1, we found that the diarylacetylenes 2 bearing an N,N-dimethylamino group on one phenyl ring and either one or preferably two ortho-oriented fluoro or chloro groups on the other phenyl ring retained the in vitro potencies in a colorectal cancer LS174T cell proliferation assay. The diarylacetylenes 2 also possessed the desired property of having minimal effects on the cardiac potassium hERG channel. Molecular docking studies suggested that diarylacetylenes and heterocyclic counterparts, like their stilbene counterparts, targeted the catalytic subunit (MAT2A) of MAT2.

We performed additional structure-activity studies with a view to obtaining improved potency, solubility and bioavailability relative to the sparingly water-soluble 4-(2,6-difluorophenyl)ethynyl)-N,N-dimethylaniline (2). Initial efforts focused on replacing the N,N-dimethylamino group in 2 with a heterocyclic ring in place of the N,N-dimethylamino group as in the heterocyclic-substituted diphenylacetylenes 4 (FIG. 1), A Sonogashira coupling of 2,6-difluorophenylacetylene (3) with 4-iodophenyl-substituted heterocycles provided access to the oxopiperidinyl, morpholino, N-methylpiperazinyl, N-pyrrolyl, and 2,5-dimethyl-N-pyrrolyl analogs 4a-4e (Table 1). The N-pyrrolyl analog 4d showed activity in a cell proliferation assay comparable to 4-((2,6-difluorophenyl)ethynyl)-N,N-dimethylaniline (2) at 1 µM concentration but considerably diminished activity at 100 nM.

Table 1 below provides inhibition of proliferation (%) of colon cancer LS174T cells for certain heterocyclic-substituted phenylethynyl benzenes of the present disclosure at various concentrations as represented by compound 4 in FIG. 1, e.g. formula (II). Table 1 also provides such data for 2,6-difluorophenyl-4'-(N,N-dimethylamino)phenylacetylene (2) for comparison.

TABLE 1

| Compound | C-4' Substituent | 10 µM | 1 µM | 100 nM |
|---|---|---|---|---|
| 2[a] | N,N-dimethylamino | | 99.5 ± 0.1 | 85.2 ± 0.5 |
| 4a | 1-piperidinyl-2-one | 68.1 ± 6.9 | 6.4 ± 11.0 | |
| 4b | N-morpholino | 32.1 ± 9.8 | 13.0 ± 2.5 | |
| 4c | N'-methyl-N-piperazinyl | 99.6 ± 0.2 | 19.9 ± 18.2 | |
| 4d | N-pyrrolyl | 96.7 ± 1.9 | 77.5 ± 9.2 | 11.0 ± 18.1 |
| 4e | 2,5-dimethyl-N-pyrrolyl | 78.8 ± 4.8 | 20.9 ± 10.0 | |

[a]data from Sviripa et al., "Halogenated diarylacetylenes repress c-myc expression in cancer cells", *Bioorg Med Chem Lett* 2014, 24:3638-40.

Because heterocyclic variants in the stilbene series in which the N,N-dimethylaniline ring in 1 (FIG. 1) was replaced by either an N,N-dimethylaminopyridine or an N,N-dimethylaminopyrimidine ring exhibited improved solubility and minimal hERG activation, we next focused on replacing the N,N-dimethylaniline ring in the diarylacetylene series with a heterocyclic ring as in the phenylethynyl-substituted heterocycles represented by compound 5 in FIG. 1, e.g., formula (III). A Sonogashira coupling of 2,6-difluorophenylacetylene with iodo-substituted heterocycles provided access to most these analogs (Table 2). In some cases, such as the synthesis of 5nn-5oo, it was preferable to couple 2,6-difluorophenylacetylene to 1-chloro-4-iodoisoquinoline and subsequently to utilize a nucleophilic aromatic substitution reaction to replace the chloro group with a secondary amine. Yet another approach involved the coupling of 2,6-difluorophenylacetylene to 1-amino-4-iodoisoquinoline to afford 4-(2,6-difluorophenyl)ethynyl)isoquinolin-1-amine and the subsequent N,N-dimethylation of the amino group using 1,2-bis[(dimethylamino)methylene]hydrazine via an intermediate 1,2,4-triazole, but this latter process proceeded in a lower overall yield than the yield in the nucleophilic aromatic substitution reaction. As summarized in Table 2, using these approaches, we synthesized 2,6-difluorophenylethynyl-substituted heterocycles including pyridines 5a-5c, pyrazine 5d, indoles 5e-5f, 1H-indazoles 5g-5k, 1H-pyrrolo[2,3-b]pyridine 5l, quinolines 5m-5ff, isoquinolines 5gg-5oo, 1,6-naphthyridine 5qq, and quinazoline 5rr.

Table 2 below provides inhibition of cell proliferation (%) of colon cancer LS174T cells by 2,6-difluorophenylethynyl-substituted heterocycles represented by compound 5 in FIG. 1, e.g. formula (III), of the present disclosure at various concentrations.

| Compound | Heterocycle or Aryl ring | Position[a] | 10 µM | 1 µM | 100 nM | 30 nM |
|---|---|---|---|---|---|---|
| 2[b] | N,N-dimethylaniline | C-4 | | 99.5 ± 0.1 | 85.2 ± 0.5 | 57 ± 1.2 |
| 5a | N,N-dimethylpyridin-3-amine | C-6 | 85.2 ± 3.8 | 68.9 ± 1.3 | 15.1 ± 7.4 | |
| 5b | N,N-dimethylpyridin-2-amine | C-5 | 83.6 ± 7.8 | 77.9 ± 7.0 | 0 ± 23.7 | |
| 5c | 2-(1H-pyrrol-1-yl)pyridine | C-5 | 95.3 ± 0.8 | 80.5 ± 6.6 | 0 ± 27.7 | |
| 5d | N,N-dimethylpyrazin-2-amine | C-5 | 91.6 ± 3.0 | 22.9 ± 9.8 | | |
| 5e | 1H-indole | C-5 | 91.5 ± 3.5 | 52.9 ± 5.9 | | |
| 5f | N-methylindole | C-5 | 95.2 ± 1.0 | 77.7 ± 13.6 | 3.0 ± 5.6 | |
| 5g | 1H-indazole | C-4 | 96.2 ± 2.0 | 19.8 ± 13.6 | | |
| 5h | 1H-indazole | C-5 | 82.9 ± 9.8 | 17.6 ± 7.9 | | |
| 5i | 1H-indazole | C-6 | 97.0 ± 1.1 | 81.5 ± 2.9 | | |
| 5j | N-methylindazole | C-5 | 94.6 ± 3.5 | 58.4 ± 9.6 | 0 ± 24.5 | |
| 5k | N-methylindazole | C-6 | 98.1 ± 0.4 | 85.9 ± 5.4 | 0 ± 22.7 | |
| 5l | 1H-pyrrolo[2,3-b]pyridine | C-5 | 77.9 ± 8.9 | 17.3 ± 12.0 | | |
| 5m | quinoline | C-2 | 93.8 ± 1.7 | 67.3 ± 13.6 | 6.1 ± 27.0 | |
| 5n | quinoline | C-3 | 90.4 ± 1.0 | 41.7 ± 6.5 | 0 ± 5.1 | |
| 5o | quinoline | C-4 | 59.0 ± 7.5 | 15.4 ± 9.1 | | |
| 5p | 2-chloroquinoline | C-3 | 85.1 ± 6.2 | 28.4 ± 10.5 | | |
| 5q | 4-chloroquinoline | C-3 | 80.4 ± 13.7 | 51.5 ± 20.4 | 0 ± 26.3 | |
| 5r | quinolin-6-amine | C-3 | 9.2 ± 15.7 | | | |
| 5s | 7-fluoroquinoline | C-3 | 95.1 ± 1.6 | 69.4 ± 4.5 | 14.8 ± 5.5 | |
| 5t | 8-fluoroquinoline | C-3 | 89.1 ± 8.2 | 63.6 ± 8.4 | 8.8 ± 5.1 | |
| 5u | 7-chloroquinoline | C-4 | 74.3 ± 0.2 | 36.0 ± 0.4 | | |
| 5v | quinoline | C-5 | 94.7 ± 2.9 | 43.1 ± 11.2 | | |
| 5w | quinoline | C-6 | 80.1 ± 1.0 | 11 ± 30.4 | | |
| 5x | quinoline | C-7 | 99.4 ± 0.3 | 90.7 ± 0.6 | 2.9 ± 14.0 | |
| 5y | quinoline | C-8 | 92.7 ± 2.9 | 47.6 ± 3.5 | | |
| 5z | 2-chloroquinoline | C-6 | 63.3 ± 2.3 | 21.2 ± 11.4 | | |
| 5aa | 4-chloroquinoline | C-6 | 89.7 ± 4.3 | 43.8 ± 10.8 | | |
| 5bb | 4-chloroquinoline | C-7 | 70.8 ± 4.8 | 23.1 ± 8.3 | | |
| 5cc | quinolin-4-amine | C-6 | 93.9 ± 0.4 | 66.2 ± 3.1 | 0 ± 5.4 | |
| 5dd | quinolin-4-amine | C-7 | 97.7 ± 2.2 | 23.6 ± 2.5 | | |
| 5ee | N,N-dimethylquinoline-2-amine | C-6 | 38.7 ± 4.3 | 2.0 ± 11.9 | | |

-continued

| Compound | Heterocycle or Aryl ring | Position[a] | 10 μM | 1 μM | 100 nM | 30 nM |
|---|---|---|---|---|---|---|
| 5ff | N,N-dimethylquinoline-4-amine | C-6 | 95.5 ± 2.0 | 81.3 ± 1.4 | 0 ± 12.9 | |
| 5gg | isoquinoline | C-1 | 96.7 ± 0.2 | 35.4 ± 15.0 | | |
| 5hh | isoquinoline | C-4 | 87.9 ± 1.0 | 16.5 ± 2.1 | | |
| 5ii | isoquinoline | C-5 | 93.6 ± 0.5 | 64.2 ± 6.1 | | |
| 5jj | isoquinoline | C-6 | 82.4 ± 10.2 | 11.6 ± 21.3 | | |
| 5kk | 1-chloroisoquinoline | C-4 | 94.0 ± 0.5 | 48.1 ± 18.1 | 0.8 ± 36.1 | |
| 5ll | 7-fluoroisoquinoline | C-1 | 96.2 ± 0.1 | 71.1 ± 3.5 | 0 ± 5.2 | |
| 5mm | isoquinolin-1-amine | C-4 | 93.1 ± 1.6 | 86.2 ± 1.6 | 35.5 ± 1.7 | |
| 5nn | N,N-dimethylisoquinolin-1-amine | C-4 | 97.6 ± 1.5 | 99.5 ± 0.1 | 81.7 ± 2.1 | 86.0 ± 2.0 |
| 5oo | N-methylisoquinolin-1-amine | C-4 | 98.9 ± 1.0 | 99.8 ± 0.2 | 99.5 ± 0.5 | 94.5 ± 1.5 |
| 5pp | 1-(4-methylpiperazin-1-yl)isoquinoline | C-4 | 100 ± 0[c] | 23.2 ± 9.4[c] | | |
| 5qq | N,N-dimethyl-1,6-naphthyridin-5-amine | C-8 | 85.2 ± 1.0 | 87.9 ± 0.8 | 59.5 ± 3.5 | |
| 5rr | quinazoline | C-7 | 96.3 ± 0.8 | 33.8 ± 4.8 | | |

[a]position of attachment of 2,6-difluorophenylethynyl group;
[b]data from Sviripa et al., "Halogenated diarylacetylenes repress c-myc expression in cancer cells", Bioorg Med Chem Lett 2014, 24: 3638-40;
[c]tested as the hydrochloride salt.

At 10 μM concentrations, most of the 2,6-difluorophenylethynyl-substituted heterocycles 5 in Table 2 displayed potent effects on LS174T colon cancer cell proliferation assays, and at 1 μM concentrations, several pyridines 5b and 5c, one indole 5f, two 1H-indazoles 5i and 5k, two quinolines 5x and 5ff, and four isoquinolines 5mm-5oo and 5qq showed greater than 75% inhibition. Two candidates that stood out with respect to potency among the 2,6-difluorophenylethynyl-substituted heterocycles 5 were 4-(2,6-difluorophenyl)ethynyl)-N,N-dimethylisoquinolin-1-amine (5nn) and 4-(2,6-difluorophenyl)ethynyl)-N-methylisoquinolin-1-amine (5oo). In addition, several of the difluorinated phenylethynyl-substituted heterocycles, such as 5pp and 5qq, furnished completely water-soluble hydrochloride salts. In summary, we identified heterocyclic variants 5 with potency and/or water solubility surpassing that of the parent compound, 4-((2,6-difluorophenyl)ethynyl)-N,N-dimethylaniline (2).

Figure 2A:
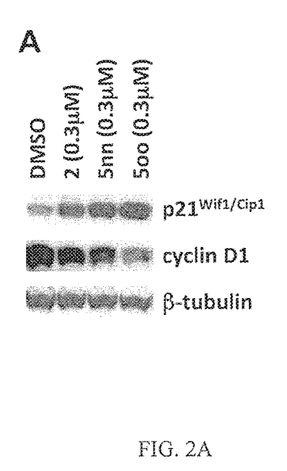
FIG. 2A is a western blot showing the effects of 4-((2,6-difluorophenyl)ethynyl)-N,N-dimethylaniline (2), 4-((2,6-difluorophenyl)ethynyl)-N,N-dimethylisoquinolin-1-amine (5nn), and 4-((2,6-difluorophenyl)ethynyl)-N-methylisoquinolin-1-amine (5oo) on the expression of cyclin D1 and p21$^{Wif1/Cip1}$ in LS174T cells at 300 nM concentrations.
Figure 2B:
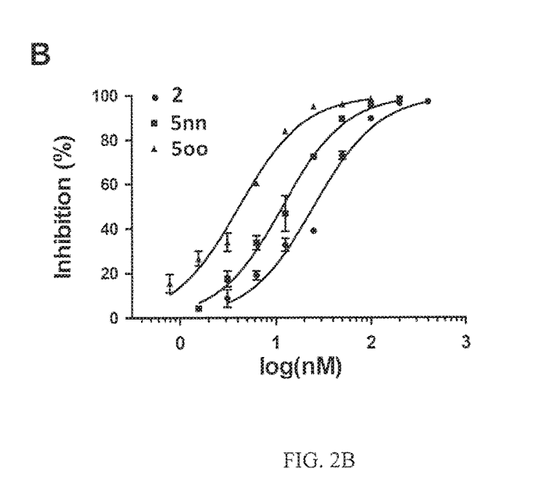
FIG. 2B is a plot of dose responses of compounds 2, 5nn and 5oo in a LS174T cell proliferation assay. IC$_{50}$ values for 2, 5nn and 5oo were 25.1±1.3, 11.8±1.5 and 4.2±0.2 nM, respectively.

Variability in a MAT2A inhibition assay using a molybdate colorimetric assay for phosphate made the measurement of cell-cycle inhibition a preferred analytical tool for assessing the potency of diarylacetylenes. We tested the effect of these heterocyclic-substituted diphenylacetylenes 4 (Table 1) and fluorinated, phenylethynyl-substituted heterocycles 5 (Table 2) on the proliferation of LS174T colon cancer cells. As shown in the western blot (FIG. 2A), the most active compounds 2, 5nn and 5oo inhibited cyclin D1 expression at 300 nM concentrations and, as expected for a cell-cycle inhibitor, induced p21$^{Wif1/Cip1}$ at the same time. Unlike the diarylacetylene series in which the N-methylanilino and N,N-dimethylanilino analogs of 2 showed comparable activity in inhibiting LS174T cell proliferation (i.e., 2, $IC_{50}$ 25.1 nM), the N-methylation pattern in the phenylethynyl-substituted heterocycles indicated that the N-methylaminoisoquinoline analog 5oo ($IC_{50}$ 4.2 nM) was more potent than the N,N-dimethylaminoisoquinoline analog 5nn ($IC_{50}$ 11.8 nM) (FIG. 2B). In summary, phenylethynyl-substituted heterocycles 5 inhibited the proliferation of LS174T colon cancer cells by altering the expression of c-myc and thereby inducing p21$^{Wif1/Cip1}$. These results are consistent with prior findings using halogenated stilbenes[1] and diarylacetylenes and given the absence of isomerization in 5 relative to stilbenes, improved potency, and improved physical properieties (e.g., water solubility), suggest that phenylethynyl-substituted hetrepress colon cancer proliferation through similar mechanisms. Additional studies of these phenylethynyl-substituted heterocycles are the subject of on-going investigations.

We also focused on phenylethynyl-substituted heterocycles represented by compound 7 in FIG. 1, e.g., formula (III). A Sonogashira coupling of 4-amino, 4-N-methylamino- or 4-N,N-dimethylaminoacetylene with iodo-substituted fluorinated heterocycles provided access to these analogs 7 (Table 3).

TABLE 3

| Compound | Heterocyclic ring | Phenyl ring | 300 nM | 100 nM | 30 nM |
|---|---|---|---|---|---|
| 7a | 2,6-difluoro-4-pyridine | $C_6H_5$ | 12.2 ± 7.1 | 24.7 ± 3.7 | 5.3 ± 7.9 |
| 7b | 2,6-difluoro-4-pyridine | $C_6H_4$-4-$NH_2$ | 36.2 ± 4.5 | 30.5 ± 2.2 | 11.4 ± 7.8 |
| 7c | 2,6-difluoro-4-pyridine | $C_6H_4$-4-$NHCH_3$ | 62.6 ± 1.3 | 49.5 ± 5.5 | 20.3 ± 5 |
| 7d | 2,6-difluoro-4-pyridine | $C_6H_4$-4-$N(CH_3)_2$ | 60.6 ± 5.2 | 20.4 ± 0.5 | 16.7 ± 7.7 |

At 300 nm concentrations, several of the 2,6-difluoro-4-pyridylethynyl-substituted benzenes 7 in Table 3 displayed potent effects on LS174T colon cancer cell proliferation assays. Potency in such in vitro tests are not the only criterion for advancing compounds forward to clinical studies, and additional studies, experimental and computational, suggested that these compounds 7 possessed minimal toxicity and improved ADME parameters. Several of these compounds 7 also showed very promising activity using in vivo xenograft studies.

EXAMPLES

The following examples are intended to illustrate further certain, preferred embodiments of the invention and are not limiting in nature. Those skilled in the art will recognize, or be able to ascertain, using no more than routine experimentation, numerous equivalents to the specific substances and procedures described herein.

Materials

Chemicals were purchased from Sigma Aldrich or Fisher Scientific or were synthesized according to literature procedures. Solvents were used from commercial vendors without further purification unless otherwise noted. Nuclear magnetic resonance spectra were determined on a Varian ($^1$H, 400 MHz; $^{13}$C, 100 Mz) and Bruker ($^1$H, 700 MHz; $^{13}$C, 176 Mz) instruments. High resolution electrospray ionization (ESI) mass spectra were recorded on a LTQ-Orbitrap Velos mass spectrometer (Thermo Fisher Scientific, Waltham, Mass., USA). The FT resolution was set at 100,000 (at 400 m/z). Samples were introduced through direct infusion using a syringe pump with a flow rate of 5 μL/min. MALDI mass spectra were obtained on a Bruker Utraflexstreme time-of-flight mass spectrometer (Billerica, Mass.), using DHB (2,5-dihydroxybenzoic acid) matrix. Purity of compounds was established by combustion analyses by Atlantic Microlabs, Inc., Norcross, Ga. Compounds were chromatographed on preparative layer Merck silica gel F254 unless otherwise indicated.

General procedure for the Sonogashira coupling of 2,6-difluorophenylacetylene with aryl iodides or heteroaryl iodides.

To a mixture of 2.1 mmol of an aryl iodide or heteroaryl iodide, 3 mmol of diisopropylethylamine, 0.02 mmol of Pd(PPh$_3$)$_4$, and 0.02 mmol of CuI in 7 mL of water was added 2 mmol of 2,6-difluorophenylacetylene. The mixture was stirred for 1-2 h at 75° C. The mixture was cooled, and the product was collected by filtration or extraction using dichloromethane. The products 4 or 5 were purified by recrystallization and/or chromatography as noted below.

1-(4-((2,6-Difluorophenyl)ethynyl)phenyl)piperidin-2-one (4a). Yield 75%; preparative layer chromatography using 1:10 methanol-dichloromethane (R$_f$=0.52); mp 148-150° C. NMR (400 MHz, DMSO-d$_6$) δ 7.58 (d, J=8.5 Hz, 2H), 7.56-7.47 (m, 1H), 7.40 (d, J=8.5 Hz, 2H), 7.26 (t, J=8 Hz, 2H), 3.64 (t, J=5.6 Hz, 2H), 2.42 (t, Jr=6.3 Hz, 2H), 1.94-1.77 (m, 4H). $^{13}$C NMR (101 MHz, DMSO-d$_6$) δ 169.01, 162.01 (dd, J=5.2, 251.5 Hz, 2C), 144.53, 131.78 (2C), 131.39 (t, J=10 Hz), 126.19 (2C), 118.35, 111.94 (dd, J=5.3, 18.2 Hz, 2C), 100.77 (t, J=19.8 Hz), 98.63 (t, J=3.1 Hz), 75.77, 50.29, 32.70, 22.91, 20.79. HRMS (ESI) calcd for C$_{19}$H$_{16}$F$_2$NO [MH+]: 312.1194. Found: 312.1195. Anal. Calcd for C$_{19}$H$_{15}$F$_2$NO: C, 73.30; H, 4.86; N, 4.50, Found: C, 73.04; H, 4.85; N, 4.52.

4-(4-((2,6-Difluorophenyl)ethynyl)phenyl)morpholine (4b). Yield 67%; column chromatography using 1:5 ethyl acetate-hexane and recrystallized from hexane; mp 144-145° C. $^1$H NMR (400 MHz, DMSO-d$_6$) δ 7.53-7.44 (m, 1H), 7.42 (d, J=8.9 Hz, 2H), 7.22 (t, J=7.9 Hz, 2H), 6.98 (d, J=8.8 Hz, 2H), 3.73 (t, J=4.8 Hz, 4H), 3.2 (t, J=4.9 Hz, 4H). $^{13}$C NMR (101 MHz, DMSO-d$_6$) δ 161.85 (dd, J=5.3, 250.6 Hz, 2C), 151.36, 132.57 (2C), 130.51 (t, J=10.1 Hz), 114.35 (2C), 111.89 (dd, J=5.4, 250.6 Hz, 2C), 110.38, 101.55 (t, J=19.9 Hz), 100.09 (t, J=3 Hz), 74.28, 65.91 (2C), 47.21 (2C). HRMS (ESI) calcd for C$_{18}$H$_{16}$F$_2$NO [MH+]: 300.1194. Found: 300.1195. Anal. Calcd for C$_{18}$H$_{15}$F$_2$NO: C, 72.23; H, 5.05; N, 4.68. Found: C, 71.98; H, 5.09; N, 4.72.

1-(4-((2,6-Difluorophenyl)ethynyl)phenyl)-4-methylpiperazine (4c). Yield 60%, preparative layer chromatography using 1:10 methanol-dichloromethane (R$_f$=0.43); mp 126-128° C. $^1$H NMR (400 MHz; DMSO-d$_6$) δ 7.53-7.42 (m, 1H), 7.39 (d, J=8.8 Hz, 2H), 7.22 (t, J=7.9 Hz, 2H), 6.96 (d, J=8.9 Hz, 2H), 3.24 (t, J=4.9 Hz, 4H), 2.43 (t, J=5.1 Hz, 4H), 2.21 (s, 3H). $^{13}$C NMR (101 MHz, DMSO-d$_6$) δ 161.82 (dd, J=5.4, 250.6 Hz, 2C), 151.21, 132.56 (2C), 130.43 (t, J=10.1 Hz), 114.49 (2C), 111.8 (dd, J=5.3, 18.2 Hz, 2C), 109.85, 101.59 (t, J=19.9 Hz), 100.22 (t, J=3 Hz), 74.17, 54.35 (2C), 46.87 (2C), 45.73. HRMS (ESI) calcd for C$_{19}$H$_{19}$F$_2$N$_2$ [MH+]: 313.1511. Found: 313.1489. Anal. Calcd for C$_{19}$H$_{18}$F$_2$N$_2$: C, 73.06; H, 5.81; N, 8.97. Found: C, 72.84; H, 5.75; N, 8.89.

1-(4-((2,6-Difluorophenyl)ethynyl)phenyl)-1H-pyrrole (4d). Yield 79%; preparative layer chromatography using 1:5 ethyl acetate-hexane (R$_f$=0.68); mp 122-124° C. $^1$H NMR (400 MHz, DMSO-d$_6$) δ 7.76-7.61 (m, 4H), 7.60-7.49 (m, 1H), 7.48 (t, J=2.2 Hz, 2H), 7.32-7.17 (m, 2H), 6.31 (t, J=2.2 Hz, 2H). $^{13}$C NMR (101 MHz, DMSO-d$_6$) δ 162.01 (dd, J=5, 251.5 Hz, two C), 140.3, 132.98 (2C), 131.36 (t, J=10.1 Hz), 119.15 (2C), 118.92 (2C), 117.61, 111.93 (dd, J=5.4, 18.3 Hz, 2C), 111.19 (2C), 100.91 (t, J=19.7 Hz), 98.45 (t, J=3 Hz), 76.09. HRMS (ESI) calcd for C$_{18}$H$_{12}$F$_2$N [MH+]: 280.0932. Found: 280.0924. Anal. Calcd for C$_{18}$H$_{11}$F$_2$N: C, 77.41; H, 3.97; N, 5.02. Found: C, 77.20; H, 4.21; N, 4.89.

1-(4-((2,6-Difluorophenyl)ethynyl)phenyl)-2,5-dimethyl-1H-pyrrole (4e). Yield 84%; column chromatography using 1:10 ethyl acetate-hexane; mp 124-126° C. $^1$H NMR (400 MHz, DMSO-d$_6$) δ 7.71 (d, J=8.4 Hz, 2H), 7.62-7.51 (m, 1H), 7.36 (d, J=8.5 Hz, 2H), 7.30-7.25 (m, 2H), 5.83 (s, 2H), 2.00 (s, 6H). $^{13}$C NMR (101 MHz, DMSO-d$_6$) δ 162.07 (dd, J=5.2, 251.8 Hz, 2C), 139.2, 132.43 (2C), 131.66 (t, J=10.2 Hz), 128.49 (2C), 127.55 (2C), 120.42, 111.96 (dd, J=5.3, 19 Hz, 2C), 106.48 (2C), 100.69 (t, J=19.7 Hz), 98.05 (t, J=3 Hz), 76.71, 12.86 (2C). HRMS (ESI) calcd for C$_{20}$H$_{16}$F$_2$N [MH+]: 308.1245, Found: 308.1229. Anal. Calcd for C$_{20}$H$_{15}$F$_2$N: C, 78.16; H, 4.92; N, 4.56. Found: C, 77.91; H, 5.03; N, 4.42.

6-((2,6-Difluorophenyl)ethynyl)-N,N-dimethylpyridin-3-amine (5a). Yield 68%; preparative layer chromatography using 1:2 ethyl acetate-hexane (R$_f$=0.53); mp 120-122° C. $^1$H NMR (400 MHz, DMSO-d$_6$) δ 8.13 (d, J=3 Hz, 1H), 7.55-7.46 (m, 1H), 7.44 (d, J=8.7 Hz, 1H), 7.29-7.2 (m, 2H), 7.06 (dd, J=3.1, 8.8 Hz, 1H), 3 (s, 6H). $^{13}$C NMR (101 MHz, DMSO-d$_6$) δ 162.01 (dd, J=5.3, 251.2 Hz, 2C), 145.52, 134.97, 130.95 (t, J=10.1 Hz), 127.79, 127.47, 117.6, 111.96 (dd, J=5.3, 18.2 Hz, 2C), 101.11 (t, J=19.8 Hz), 99.79 (t, J=3.1 Hz), 72.88, 39.33 (2C). HRMS (ESI) calcd for C$_{15}$H$_{13}$F$_2$N$_2$ [MH+]: 259.1041. Found: 259.1023. Anal. Calcd for C$_{15}$H$_{12}$F$_2$N$_2$: C, 69.76; H, 4.68; N, 10.85. Found: C, 69.61; H, 4.85; N, 10.83.

5-((2,6-Difluorophenyl)ethynyl)-N,N-dimethylpyridin-2-amine (5b). Yield 79%; preparative layer chromatography using 1:5 ethyl acetate-hexane (R$_f$=0.41); mp 110-112° C. $^1$H NMR (700 MHz, DMSO-d$_6$) δ 8.29 (d, J=2.1 Hz, 1H), 7.64 (dd, J=2.4, 8.9 Hz, 1H), 7.53-7.43 (m, 1H), 7.22 (t, J=7.9 Hz, 2H), 6.68 (d, J=8.9 Hz, 1H), 3.08 (s, 6H). $^{13}$C NMR (176 MHz, DMSO-d$_6$) δ 161.74 (dd, J=5.2, 250.7 Hz, 2C), 158.12, 150.93, 139.51, 130.56 (t, J=10.1. Hz), 111.81 (dd, J=3.9, 20.2 Hz, 2C), 105.54, 104.57, 101.48 (t, J=19.8 Hz), 98.02 (t, J=3 Hz), 76.11, 37.52 (2C). HRMS (ESI) calcd for C$_{15}$H$_{13}$F$_2$N$_2$ [MH+]: 259.1041. Found: 259.1023. Anal. Calcd for C$_{15}$H$_{12}$F$_2$N$_2$: C, 69.76; H, 4.68; N, 10.85. Found: C, 69.49; H, 4.81; N, 10.76.

5-((2,6-Difluorophenyl)ethynyl)-2-(1H-pyrrol-1-yl)pyridine (5c). Yield 66%, preparative layer chromatography using 1:5 ethyl acetate-hexane (R$_f$=0.47) and recrystallization from abs. ethanol; mp 121-123° C. $^1$H NMR (700 MHz DMSO-d$_6$) δ 8.63 (d, J=2.2 Hz, 1H), 8.12 (dd, J=2.3, 8.6 Hz, 1H), 7.81 (d, J=8.6 Hz, 1H), 7.73 (t, J=2.3 Hz, 2H), 7.62-7.51 (m, 1H), 7.28 (t, J=8 Hz, 2H), 6.34 (t, J=2.3 Hz, 2H). $^{13}$C NMR (176 MHz, DMSO-d$_6$) δ 162.02 (dd, J=5, 252 Hz, 2C), 151.04, 150.19, 141.74, 131.8 (t, J=10.1 Hz), 118.35 (2C), 114.63, 112.07 (m, 4C), 111.27, 100.54 (t, J=19.7 Hz), 95.5 (t, J=2.9 Hz), 78.6. HRMS (ESI) calcd for $C_{17}H_{11}F_2N_2$ [MH+]: 280.0885. Found: 280.0886. Anal. Calcd for $C_{17}H_{10}F_2N_2$: C, 72.85; H, 3.60; N, 10.00. Found: C, 72.74; H, 3.69; N, 9.84.

5-((2,6-Difluorophenyl)ethynyl)-N,N-dimethylpyrazin-2-amine (5d). Yield 73%, column chromatography using 1:10 ethyl acetate-hexane; mp 137-138° C. $^1$H NMR (400 MHz, DMSO-$d_6$) δ 8.3 (d, J=1.4 Hz, 1H), 8.19 (d, J=1.4 Hz, 1H), 7.52 (m, 1H), 7.25 (t, J=8 Hz, 2H), 3.13 (s, 6H). $^{13}$C NMR (101 MHz, DMSO-$d_6$) δ 161.93 (dd, J=251.5, 5.2 Hz, 2C), 152.96, 145.35, 131.25 (t, J=10.1 Hz), 130.64, 123.25, 111.93 (dd, J=5.2, 18.6 Hz, 2C), 100.85 (t, J=19.8 Hz), 97.31 (t, J=3 Hz), 75.74, 37.2 (2C). HRMS (ESI) calcd for $C_{14}H_{12}F_2N_3$ [MH+]: 260.0994. Found: 260.0994. Anal. Calcd for $C_{14}H_{11}F_2N_3$: C, 64.86; H, 4.28; N, 16.21. Found: C, 64.63; 4.25; N, 16.39.

5-((2,6-Difluorophenyl)ethynyl)-1H-indole (5e). Yield 63%; preparative layer chromatography using 1:5 ethyl acetate-hexane ($R_f$=0.44); mp 131-133° C. $^1$H NMR (400 MHz, DMSO-$d_6$) δ 11.4 (s, 1H), 7.82 (s, 1H), 7.52-7.44 (m, 3H), 7.27 (dd, J=1.6, 8.5 Hz, 1H), 7.23 (t, J=8 Hz, 2H), 6.51-6.49 (m, 1H). $^{13}$C NMR (101 MHz, DMSO-$d_6$) δ 161.94 (dd, J=5.4, 250.5 Hz, 2C), 136.08, 130.44 (t, J=10.1 Hz), 127.63, 126.95, 124.24, 124.18, 112.06, 111.81 (dd, J=5.4, 18.3 Hz, 2C), 111.35, 101.69 (t, J=19.7 Hz), 101.59, 101.49 (t, J=3 Hz), 73.26. HRMS (ESI) calcd for $C_{16}H_{10}F_2N$ [MH+]: 254.0776. Found: 254.0760. Anal. Calcd for $C_{16}H_9F_2N$: C, 75.88; H, 3.58; N, 5.53. Found: C, 76.07; H, 3.63; N, 5.41.

5-((2,6-Difluorophenyl)ethynyl)-1-methyl-1H-indole (5f). Yield 76%; column chromatography using 1:2 ethyl acetate-hexane; trip 100-102° C. $^1$H NMR (400 MHz, DMSO-$d_6$) δ 7.82 (d, J=1.6 Hz, 1H) 7.55-7.45 (m, 2H), 7.43 (d, J=3 Hz, 1H), 7.33 (dd, J=1.6, 8.5 Hz, 1H), 7.24 (t, J=7.9 Hz, 2H), 6.5 (d, J=2.6 Hz, 1H), 3.82 (s, 3H). $^{13}$C NMR (101 MHz, DMSO-$d_6$) δ 161.94 (dd, J=5.4, 250.6 Hz, 2C), 136.45, 131.28, 130.51 (t, J=10.1 Hz), 127.96, 124.41, 124.24, 111.83 (dd, J=5.3, 19.6 Hz, 2C), 111.45, 110.42, 101.63 (t, J=20.0 Hz), 101.28 (t, J=3 Hz), 100.92, 73.52, 32.63. HRMS (ESI) calcd for $C_{17}H_{12}F_2N$ [MH+]: 268.0932. Found: 268.0917. Anal. Calcd for $C_{17}H_{11}F_2N$: C, 76.39; H, 4.15; N, 5.24. Found: C, 76.17; H, 4.31; N, 5.04.

4-((2,6-Difluorophenyl)ethynyl)-1H-indazole (5g). Yield 71%, column chromatography using 1:2 ethyl acetate-hexane; mp 178-179° C. $^1$H NMR (400 MHz, DMSO-$d_6$) δ 13.45 (s, 1H), 8.11 (s, 1H), 7.69 (d, J=7.8 Hz, 1H), 7.63-7.52 (m, 1H), 7.47-7.37 (m, 2H), 7.3 (t, J=8 Hz, 2H). $^{13}$C NMR (101 MHz, DMSO-$d_6$) δ 162.05 (dd, J=5.2, 251.8 Hz, 2C), 139.64, 132.2, 131.67 (t, J=10.2 Hz), 126.16, 124.5, 123.35, 112.98, 112.22, 112.05 (dd, J=5.3, 18.2 Hz, 2C), 100.9 (t, J=19.7 Hz), 96.74 (t, J=3 Hz), 79.12, HRMS (ESI) calcd for $C_{15}H_9F_2N_2$ [MH+]: 255.0728. Found: 255.0712. Anal. Calcd for $C_{15}H_8F_2N_2$: C, 70.86; H, 3.17; N, 11.02. Found: C, 70.60; H, 3.25; N, 10.92.

5-((2,6-Difluorophenyl)ethynyl)-1H-indazole (5h). Yield 25%, preparative layer chromatography using 1:2 ethyl acetate-hexane ($R_f$=0.63); mp 193-195° C. $^1$H NMR (700 MHz, DMSO-$d_6$) δ 13.34 (s, 1H), 8.15 (s, 1H), 8.08 (s, 1H), 7.62 (d, J=8.6 Hz, 1H), 7.54-7.45 (m, 2H), 7.25 (t, J=7.9 Hz, 2H). $^{13}$C NMR (176 MHz, DMSO-$d_6$) δ 162.01 (dd, J=5.2, 251 Hz, 2C), 139.52, 134.15, 130.94 (t, J=10.1 Hz), 128.85, 124.98, 122.82, 112.96, 111.88 (dd, J=3.8, 20.2 Hz, 2C), 110.94, 101.24 (t, J=19.8 Hz), 100.03 (t, J=3 Hz), 74.15. HRMS (ESI) calcd for $C_{15}H_9F_2N_2$ [MH+]: 255.0728. Found: 255.0727. Anal. Calcd for $C_{15}H_8F_2N_2$: C, 70.86; H, 3.17; N, 11.02, Found: C, 70.64; H, 3.22; N, 11.09.

6-((2,6-Difluorophenyl)ethynyl)-1H-indazole (5i). Yield 87%, column chromatography using 1:1 ethyl acetate-hexane; mp 192-194° C. $^1$H NMR (400 MHz, DMSO-$d_6$) δ 13.31 (s, 1H), 8.15 (s, 1H), 7.85 (d, J=8.3 Hz, 1H), 7.77 (s, J=1.2 Hz, 1H), 7.6-7.48 (m, 1H), 7.33-7.21 (m, 3H). $^{13}$C NMR (101 MHz, DMSO-$d_6$) δ 162.09 (dd, J=5.2, 251.5 Hz, 2C), 139.31, 133.87, 131.44 (t, J=10.2 Hz), 123.20, 123.04, 121.37, 118.43, 113.63, 111.99 (dd, J=5.3, 19 Hz, 2C), 100.94 (t, J=19.7 Hz), 99.67 (t, J=3.1 Hz), 75.66. HRMS (ESI) calcd for $C_{15}H_9F_2N_2$ [MH+]: 255.0728. Found: 255.0712. Anal. Calcd for $C_{15}H_8F_2N_2$: C, 70.86; H, 3.17; N, 11.02. Found: C, 70.61; H, 3.06; N, 10.88.

5-((2,6-difluorophenyl)ethynyl)-1-methyl-1H-indazole (5j). Yield 47%; preparative layer chromatography using 1:5 ethyl acetate-hexane ($R_f$=0.31); mp 107-109° C. $^1$H NMR (700 MHz, DMSO-$d_6$) δ 8.12 (d, J=0.9 Hz, 1H), 8.06 (s, 1H), 7.73 (d, J=8.7 Hz, 1H), 7.55 (dd, J=1.5, 8.7 Hz, 1H), 7.53-7.48 (m, 1H), 7.25 (t, J=7.9 Hz, 2H), 4.08 (s, 3H). $^{13}$C NMR (176 MHz, DMSO-$d_6$) δ 162.01 (dd, J=5.2, 251.0 Hz, 2C), 139.19, 133.06, 130.98 (t, J=10 Hz), 128.78, 125.17, 123.39, 113.04, 111.89 (dd, J=3.8, 20.2 Hz, 2C), 110.54, 101.2 (t, J=19.8 Hz), 99.87 (t, J=3 Hz), 74.38, 35.53. HRMS (ESI) calcd for $C_{16}H_{11}F_2N_2$ [MH+]: 269.0885. Found: 269.0885. Anal. Calcd for $C_{16}H_{10}F_2N_2$: C, 71.64; H, 3.76; N, 10.44. Found: C, 71.41; H, 3.75; N, 10.53.

6-((2,6-Difluorophenyl)ethynyl)-1-methyl-1H-indazole (5k). Yield 75%; preparative layer chromatography using 1:5 ethyl acetate-hexane ($R_f$=0.35); mp 117-119° C. $^1$H NMR (400 MHz, DMSO-$d_6$) δ 8.12 (s, 1H), 7.99 (s, 1H), 7.83 (d, J=8.4 Hz, 1H), 7.63-7.47 (m, 1H), 7.32-7.2 (m, 3H), 4.09 (s, 3H). $^{13}$C NMR (101 MHz, DMSO-$d_6$) δ 162.09 (dd, J=5.2, 251.6 Hz, 2C), 139.09, 132.68, 131.44 (t, J=10.2 Hz), 123.56, 123.20, 121.49, 118.42, 113.46, 111.94 (dd, J=5.2, 18.6 Hz, 2C), 100.88 (t, J=19.7 Hz), 99.65 (t, J=3 Hz), 75.81, 35.58, HRMS (ESI) calcd for $C_{16}H_{11}F_2N_2$ [MH+]: 269.0885. Found: 269.0886. Anal. Calcd for $C_{16}H_{10}F_2N_2$: C, 71.64; H, 3.76; N, 10.44. Found: C, 71.48; H, 3.83; N, 10.39.

5-((2,6-Difluorephenyl)ethynyl)-1H-pyrrolo[2,3-b]pyridine (5l). Yield 45%; column chromatography using 1:2 ethyl acetate-hexane; mp 192-194° C. $^1$H NMR (400 MHz, DMSO-$d_6$) δ 11.99 (s, 1H), 8.41 (d, J=2 Hz, 1H), 8.22 (d, J=2 Hz, 1H), 7.59 (t, J=3 Hz, 1H), 7.57-7.47 (m, 1H), 7.26 (t, J=8 Hz, 2H), 6.52 (dd, J=1.8, 3.5 Hz, 1H). $^{13}$C NMR (101 MHz, DMSO-$d_6$) δ 161.95 (dd, J=5.2, 251.2 Hz, 2C), 147.80, 145.04, 131.21, 131.02 (t, J=10.3 Hz), 127.83, 119.20, 111.76 (dd, J=5, 19 Hz, 2C), 109.53, 101.29 (t, J=19.9 Hz), 100.42, 98.22 (t, J=3 Hz), 75.88. HRMS (ESI) calcd for $C_{15}H_9F_2N_2$ [MH+]: 255.0728. Found: 255.0710. Anal. Calcd for $C_{15}H_8F_2N_2$: C, 70.86; H, 3.17; N, 11.02. Found: C, 70.57; H, 3.17; N, 10.88.

2-((2,6-Difluorophenyl)ethynyl)quinoline (5m). Yield 83%; column chromatography using 1:5 ethyl acetate-hexane; mp 127-129° C. $^1$H NMR (400 MHz, DMSO-$d_6$) δ 8.48 (d, J=8.5 Hz, 1H), 8.09-8.02 (m, 2H), 7.89-7.82 (m, 1H), 7.76 (d, J=8.4 Hz, 1H), 7.72-7.66 (m, 1H), 7.66-7.58 (m, 1H), 7.32 (t, J=8.1 Hz, 2H). $^{13}$C NMR (101 MHz, DMSO-$d_6$) δ 162.44 (dd, J=5, 252.8 Hz, 2C), 147.66, 141.73, 137.07, 132.57 (t, J=10.2 Hz), 130.62, 128.75, 128.05, 127.82, 127.15, 124.25, 112.16 (dd, J=4.6, 19 Hz, 2C), 99.97 (t, J=19.7 Hz), 98.51 (t, J=3 Hz), 75.62. HRMS (ESI) calcd for $C_{17}H_{10}F_2N$ [MH+]: 266.0776. Found: 266.0756. Anal. Calcd for $C_{17}H_9F_2N$: C, 76.98; H, 3.42; N, 5.28. Found: C, 76.73; H, 3.38; N, 5.17.

3-((2,6-Difluorophenyl)ethynyl)quinoline (5n). Yield 64%; preparative layer chromatography using 1:10 ethyl acetate-hexane ($R_f$=0.42); mp 115-117° C. $^1$H NMR (400

MHz, DMSO-d$_6$) δ 9 (d, J=2.1 Hz, 1H), 8.72 (d, J=2.2 Hz, 1H), 8.06 (d, J=8.4 Hz, 2H), 7.85 (t, J=7.6 Hz, 1H), 7.69 (t, J=7.6 Hz, 1H), 7.64-7.52 (m, 1H), 7.30 (t, J=8.1 Hz, 2H). $^{13}$C NMR (101 MHz, DMSO-d$_6$) δ 162.12 (dd, J=5, 252.2 Hz, 2C), 151.13, 146.64, 139.13, 132.02 (t, J=10.2 Hz), 131.04, 128.87, 128.29, 127.7, 126.73, 115.41, 112.06 (dd, J=5, 18.7 Hz, 2C), 100.46 (t, J=19.7 Hz), 96.21 (t, J=3.1 Hz), 78.9. HRMS (ESI) calcd for C$_{17}$H$_{10}$F$_2$N [MH+]: 266.0776. Found: 266.0757. Anal. Calcd for C$_{17}$H$_9$F$_2$N; C, 76.98; H, 3.42; N, 5.28. Found: C, 76.68; H, 3.50; N, 5.11.

4-((2,6-Difluorophenyl)ethynyl)quinoline (5o). Yield 68%; column chromatography using 1:5 ethyl acetate-hexane; mp 101-102° C. $^1$H NMR (400 MHz, DMSO-d$_6$) δ 8.97 (d, J=4.4 Hz, 1H), 8.29 (d, J=8.1 Hz, 1H), 8.12 (d, J=8.3 Hz, 1H), 7.95-7.84 (m, 1H), 7.83-7.75 (m, 2H), 7.70-7.58 (m, 1H), 7.34 (t, J=8.1 Hz, 2H). $^{13}$C NMR (101 MHz, DMSO-d$_6$) δ 162.22 (dd, J=4.9, 252.9 Hz, 2C), 150.26, 147.50, 132.8 (t, J=10.2 Hz), 130.44, 129.78, 128.15, 127.1, 126.35, 124.97, 123.86, 112.21 (dd, J=5.3, 19 Hz, 2C), 100.06 (t, J=19.8 Hz), 94.17 (t, J=3 Hz), 84.92. HRMS (ESI) calcd for C$_{17}$H$_{10}$F$_2$N [MH+]: 266.0776. Found: 266.0757, Anal. Calcd for C$_{17}$H$_9$F$_2$N: C, 76.98; H, 3.42; N, 5.28. Found: C, 77.21; H, 3.43; N, 5.24.

2-Chloro-3-((2,6-difluorophenyl)ethynyl)quinoline (5p). Yield 53%; column chromatography using 1:5 ethyl acetate-hexane; mp 137-138° C. $^1$H NMR (400 MHz, DMSO-d$_6$) δ 8.89 (s, 1H), 8.1 (d, J=8.2 Hz, 1H), 8 (d, J=8.5 Hz, 1H), 7.93-7.84 (m, 1H), 7.77-7.69 (m, 1H), 7.68-7.56 (m, 1H), 7.31 (t, J=8.1 Hz, 2H). $^{13}$C NMR (101 MHz, DMSO-d$_6$) δ 162.2 (dd, J=5, 252.8 Hz, 2C), 148.86, 146.09, 143, 132.47 (t, J=10.1 Hz), 132.3, 128.28, 128.16, 127.84, 126.14, 115.72, 112.17 (dd, J=4.5, 19 Hz, 2C), 100.22 (t, J=19.7 Hz), 94.07 (t, J=2.9 Hz), 82.23. HRMS (ESI) calcd for C$_{17}$H$_9$ClF$_2$N [MH+]: 300.0386. Found: 300.0368. Anal. Calcd for C$_{17}$H$_8$ClF$_2$N: C, 68.13; H, 2.69; N, 4.67. Found: C, 68.16; H, 2.73; N, 4.38.

4-Chloro-3-((2,6-difluorophenyl)ethynyl)quinoline (5q). Yield 40%; recrystallized from methanol; mp 140-142° C. $^1$H NMR (400 MHz, DMSO-d$_6$) δ 9.03 (s, 1H), 8.27 (d, J=8.4 Hz, 1H), 8.14 (d, J=8.4 Hz, 1H), 7.94 (t, J=7.7 Hz, 1H), 7.84 (t, J=7.7 Hz, 1H), 7.7-7.56 (m, 1H), 7.32 (t, J=8.2 Hz, 2H). $^{13}$C NMR (101 MHz, DMSO-d$_6$) δ 162.11 (dd, J=4.9, 253.1 Hz, 2C), 151.25, 147.27, 143, 132.62 (t, J=10.2 Hz), 131.84, 129.65, 129.22, 124.83, 124.17, 115.77, 112.16 (dd, J=4.6, 19 Hz, 2C), 100.15 (t, J=19.7 Hz), 93.43 (t, J=3 Hz), 84.18. HRMS (ESI) calcd for C$_{17}$H$_9$ClF$_2$N [MH+]: 300.0386. Found: 300.0366. Anal. Calcd for C$_{17}$H$_8$ClF$_2$N: C, 68.13; H, 2.69; N, 4.67. Found: C, 67.84; H, 2.82; N, 4.53.

3-((2,6-Ditfluorophenyl)ethynyl)quinolin-6-amine (5r). Yield 67%; column chromatography using 2:1 ethyl acetate-hexane; mp 184-185° C. $^1$H NMR (400 MHz, DMSO-d$_6$) δ 8.54 (d, J=2.1 Hz, 1H), 8.26 (d, J=2.1 Hz, 1H), 7.73 (d, J=9 Hz, 1H), 7.63-7.51 (m, 1H), 7.29 (t, J=8 Hz, 2H), 7.22 (dd, J=2.4, 9 Hz, 1H), 6.83 (d, J=2.5 Hz, 1H), 5.82 (s, 2H). $^{13}$C NMR (101 MHz, DMSO-d$_6$) δ 162.10 (dd, J=5.1, 251.9 Hz, 2C), 148.05, 145.57, 140.98, 135.88, 131.76 (t, J=10.2 Hz), 129.62, 128.76, 123, 115.13, 112.07 (dd, J=5, 18.7 Hz, 2C), 104.41, 100.8 (t, J=19.7 Hz), 97.1 (t, J=3 Hz), 78.02. HRMS (ESI) calcd for C$_{17}$H$_{11}$F$_2$N$_2$ [MH+]: 281.0885. Found: 281.0864. Anal. Calcd for C$_{17}$H$_{10}$F$_2$N$_2$: C, 72.85; H, 3.60; N, 10.00. Found: C, 72.57; H, 3.64; N, 9.84.

3-((2,6-Difluorophenyl)ethynyl)-7-fluoroquinoline (5s). Yield 87%; column chromatography using 1:5 ethyl acetate-hexane; mp 142-143° C. $^1$H NMR (400 MHz, DMSO-d$_6$) δ 9.03 (d, J=2 Hz, 1H), 8.77 (d, J=2.1 Hz, 1H), 8.17 (dd, J=6.3, 9.1 Hz, 1H), 7.83 (dd, J=2.5, 10.3 Hz, 1H), 7.66 (td, J=2.6, 8.9 Hz, 1H), 7.61-7.54 (m, 1H), 7.3 (t, J=8.1 Hz, 2H). $^{13}$C NMR (101 MHz, DMSO-d$_6$) δ 163.16 (d, J=250.1 Hz), 162.12 (dd, J=5.1, 252.3 Hz, 2C), 152.29, 147.61 (d, J=13 Hz), 139.24 (d, J=1.3 Hz), 132.07 (t, J=10.2 Hz), 131.14 (d, J=10.3 Hz), 124.09, 118.13 (d, J=25.5 Hz), 114.95 (d, J=2.7 Hz), 112.58 (d, J=20.6 Hz), 112.10 (dd, J=5.3, 18.9 Hz, 2C), 100.4 (t, J=19.7 Hz), 95.94 (t, J=2.9 Hz), 78.94. HRMS (ESI) calcd for C$_{17}$H$_9$F$_3$N [MH+]: 284.0682. Found: 284.0661. Anal. Calcd for C$_{17}$H$_8$F$_3$N: C, 72.09; H, 2.85; N, 4.95. Found: C, 71.83; H, 2.94; N, 4.70.

3-((2,6-Difluorophenyl)ethynyl)-8-fluoroquinoline (5t). Yield 79%; recrystallized from methanol; mp 136-137° C. $^1$H NMR (400 MHz, DMSO-d$_6$) δ 9.05 (d, J=2 Hz, 1H), 8.8 (s, 1H), 7.97-7.84 (m, 1H), 7.75-7.65 (m, 2H), 7.64-7.56 (m, 1H), 7.31 (t, J=8.1 Hz, 2H). $^{13}$C NMR (101 MHz, DMSO-d$_6$) δ 162.15 (dd, J=5, 252.4 Hz, 2C), 157.08 (d, J=255.6 Hz), 151.38 (d, J=1.5 Hz), 139.04 (d, J=2.9 Hz), 136.37 (d, J=12 Hz), 132.25 (t, J=10.2 Hz), 128.44 (d, J=2 Hz), 127.91 (d, J=8 Hz), 124.26 (d, J=4.6 Hz), 116.55, 115.22 (d, J=18.4 Hz), 112.11 (dd, J=5, 18.6 Hz, 2C), 100.27 (t, J=19.7 Hz), 95.71 (t, J=3 Hz), 79.59. HRMS (ESI) calcd for C$_{17}$H$_9$F$_3$N [MH+]: 284.0682. Found: 284.0661. Anal. Calcd for C$_{17}$H$_8$F$_3$N: C, 72.09; H, 2.85; N, 4.95. Found; C, 71.79; H, 2.92; N, 4.95.

7-Chloro-4-((2,6-difluorophenyl)ethynyl)quinoline (5u). Yield 80%; column chromatography in 1:150 methanol-dichloromethane; mp 130-132° C., $^1$H NMR (400 MHz, DMSO-d$_6$) δ 8.99 (d, J=4.4 Hz, 1H), 8.25 (d, J=8.9 Hz, 1H), 8.17 (d, J=2.1 Hz, 1H), 7.83 (dd, J=2.1, 8.9 Hz, 1H), 7.80 (d, J=4.5 Hz, 1H), 7.7-7.59 (m, 1H), 7.34 (t, J=8.2 Hz, 2H). $^{13}$C NMR (101 MHz, DMSO-d$_6$) δ 162.24 (dd, J=4.9, 253.1 Hz, 2C), 151.62, 147.83, 135.06, 133.04 (t, J=10.3 Hz), 128.78, 128.42, 127.32, 127.01, 125.05, 124.22, 112.24 (dd, J=4.5, 19 Hz, 2C), 99.89 (t, J=19.6 Hz), 93.66 (t, J=3 Hz), 85.43. HRMS (ESI) calcd for C$_{17}$H$_9$ClF$_2$N [MH+]: 300.0386. Found: 300.0366. Anal. Calcd for C$_{17}$H$_8$ClF$_2$N: C, 68.13; H, 2.69; N, 4.67. Found: C, 67.96; H, 2.68; N, 4.68.

5-((2,6-Difluorophenyl)ethynyl)quinoline (5v). Yield 68%; preparative layer chromatography using 1:10 ethyl acetate-hexane (R$_f$=0.45); mp 98-100° C. $^1$H NMR (400 MHz, DMSO-d$_6$) δ 9.04-9 (m, 1H), 8.64 (d, J=8.2 Hz, 1H), 8.15 (dd, J=2.5, 8.5 Hz, 1H), 7.94 (dd, J=2.8, 7.2 Hz, 1H), 7.9-7.78 (m, 1H), 7.78-7.69 (m, 1H), 7.66-7.52 (m, 1H), 7.40-7.23 (m, 2H). $^{13}$C NMR (101 MHz, DMSO-d$_6$) δ 162.06 (dd, J=5.1, 251.9 Hz, 2C), 151.47, 147.34, 133.17, 131.9 (t, J=10.2 Hz), 131.13, 131.06, 129.35, 127.62, 122.86, 119.2, 112.06 (dd, J=5.3, 18.3 Hz, 2C), 100.56 (t), 95.63 (t, J=3.1 Hz), 81.48. HRMS (ESI) calcd for C$_{17}$H$_{10}$F$_2$N [MH+]: 266.0776. Found: 266.0758. Anal. Calcd for C$_{17}$H$_9$F$_2$N: C, 76.98; H, 3.42; N, 5.28. Found: C, 76.80; H, 3.47; N, 5.15.

6-((2,6-Difluorophenyl)ethynyl)quinoline (5w). Yield 80%; column chromatography using 1:2 ethyl acetate-hexane; mp 91-93° C. $^1$H NMR (400 MHz, DMSO-d$_6$) δ 8.96 (dd, J=1.8, 4.2 Hz, 1H), 8.44 (d, J=8.1 Hz, 1H), 8.33 (d, J=1.9 Hz, 1H), 8.07 (d, J=8.7 Hz, 1H), 7.86 (dd, J=1.9, 8.7 Hz, 1H), 7.61 (dd, J=4.2, 8.3 Hz, 1H), 7.59-7.52 (m, 1H), 7.29 (t, J=8.1 Hz, 2H). $^{13}$C NMR (101 MHz, DMSO-d$_6$) δ 162.12 (dd, J=5.1, 251.9 Hz, 2C), 151.86, 147.35, 136.13, 132.05, 131.74 (t, J=10.2 Hz), 131.38, 129.7, 127.75, 122.44, 119.23, 112.01 (dd, J=4.9, 18.7 Hz, 2C), 100.67 (t, J=19.7 Hz), 98.47 (t, J=3 Hz), 76.91. HRMS (ESI) calcd for C$_{17}$H$_{10}$F$_2$N [MH+]: 266.0776. Found: 266.0758. Anal. Calcd for C$_{17}$H$_9$F$_2$N: C, 76.98; H, 3.42; N, 5.28. Found: C, 76.97; H, 3.33; N, 5.29.

7-((2,6-Difluorophenyl)ethynyl)quinoline (5x). Yield 74%; preparative layer chromatography using 1:10 ethyl acetate-hexane ($R_f$=0.49); mp 123-125° C. $^1$H NMR (400 MHz, DMSO-$d_6$) δ 8.98 (dd, J=1.7, 4.2 Hz, 1H), 8.43 (d, J=8.2 Hz, 1H), 8.21 (d, J=1.1 Hz, 1H), 8.07 (d, J=8.4 Hz, 1H), 7.73 (dd, J=1.6, 8.4 Hz, 1H), 7.66-7.5 (m, 2H), 7.29 (t, J=8.1 Hz, 2H). $^{13}$C NMR (101 MHz, DMSO-$d_9$) δ 162.13 (dd, J=5, 252 Hz, 2C), 151.81, 147.12, 136.01, 132.15, 131.86 (t, J=10.2 Hz), 129.08, 128.46, 128.24, 122.56, 122.21, 112.7-111.37 (dd, J=5, 18.6 Hz, 2C), 100.62 (t, J=19.8 Hz), 98.35 (t, J=3.1 Hz), 77.65. HRMS (ESI) calcd for $C_{17}H_{10}F_2N$ [MH+]: 266.0776. Found: 266.0757. Anal. Calcd for $C_{17}H_9F_2N$: C, 76.98; H, 3.42; N, 5.28. Found: C, 77.15; H, 3.28; N, 5.31.

8-((2,6-Difluorophenyl)ethynyl)quinoline (5y). Yield 62%; column chromatography using 1:5 ethyl acetate-hexane; mp 108-110° C. $^1$H NMR (400 MHz, DMSO-$d_6$) δ 9.04 (dd, J=1.8, 4.2 Hz, 1H), 8.47 (dd, J=1.8, 8.3 Hz, 1H), 8.11 (d, J=8.2 Hz, 1H), 8.08 (dd, J=1.4, 7.2 Hz, 1H), 7.7-7.62 (m, 2H), 7.6-7.5 (m, 1H), 7.28 (t, J=8 Hz, 2H). $^{13}$C NMR (101 MHz, DMSO-$d_6$) δ 162.07 (dd, J=5.2, 251.6 Hz, 2C), 151.47, 147.17, 136.71, 134.39, 131.37 (t, J=10.2 Hz), 130, 128.02, 126.3, 122.36, 121.25, 111.94 (dd, J=5.3, 19 Hz, 2C), 101.33 (t, J=19.6 Hz), 97.3 (t, J=3 Hz), 80.76. HRMS (ESI) calcd for $C_{17}H_{10}F_2N$ [MH+]: 266.0776. Found: 266.0757. Anal. Calcd for $C_{17}H_9F_2N$: C, 76.98; H, 3.42; N, 5.28. Found: C, 76.68; H, 3.30; N, 5.29.

2-Chloro-6-((2,6-difluorophenyl)ethynyl)quinoline (5z). Yield 67%; column chromatography using 1:5 ethyl acetate-hexane; mp 137-138° C. $^1$H NMR (400 MHz, DMSO-$d_6$) δ 8.51 (d, J=8.7 Hz, 1H), 8.39 (s, 1H), 8 (d, J=8.7 Hz, 1H), 7.92 (dd, J=8.7, 1.6 Hz, 1H), 7.69 (d, J=8.6 Hz, 1H), 7.63-7.53 (m, 1H), 7.29 (t, J=8.1 Hz, 2H). $^{13}$C NMR (100 MHz, DMSO-$d_6$) δ 162.14 (dd, J=252, 5.1 Hz, 2C), 151.17, 146.89, 140.01, 132.81, 131.97, 131.93 (t, J=10.2 Hz), 128.64, 126.69, 123.53, 119.89, 112.06, (dd, J=5.3, 19 Hz, 2C), 100.54 (t, J=19.8 Hz), 98.05 (t, J=3 Hz). 77.38. HRMS (ESI) calcd for $C_{17}H_9ClF_2N$ [MH+]: 300.0386. Found: 300.0366. Anal. Calcd for $C_{17}H_8ClF_2N$: C, 68.13; H, 2.69; N, 4.67. Found: C, 67.93; H, 2.70; N, 4.49.

4-Chloro-6-((2,6-difluorophenyl)ethynyl)quinoline (5aa). Yield 64%; preparative layer chromatography using 1:5 ethyl acetate-hexane ($R_f$=0.33) and recrystallization from hexane; mp 120-122° C. $^1$H NMR (700 MHz, DMSO-$d_6$) δ 8.89 (d, J=4.7 Hz, 1H), 8.33 (d, J=1.8 Hz, 1H), 8.14 (d, J=8.6 Hz, 1H), 7.96 (dd, J=1.8, 8.6 Hz, 1H), 7.84 (d, J=4.7 Hz, 1H), 7.67-7.5 (m, 1H), 7.29 (t, J=8 Hz, 2H), $^{13}$C NMR, (176 MHz, DMSO-$d_6$) δ 162.14 (dd, J=4.9, 252.3 Hz, 2C), 151.75, 148.13, 140.97, 132.55, 132 (t, J=10.1 Hz), 130.46, 127.06, 125.49, 122.61, 120.88, 112.00 (dd, J=3.8, 20.1 Hz, 2C), 100.41 (t, J=19.7 Hz), 97.85 (t, J=3 Hz), 77.94. HRMS (ESI) calcd for $C_{17}H_9ClF_2N$ [MH+]: 300.0386, Found: 300.0389. Anal. Calcd for $C_{17}H_8ClF_2N$: C, 68.13; H, 2.69; N, 4.67, Found: C, 67.85; H, 2.79; N, 4.53.

4-Chloro-7-((2,6-difluorophenyl)ethynyl)quinoline (5bb). Yield 63%; column chromatography using 1:5 ethyl acetate-hexane and recrystallized from acetonitrile; mp 148-150° C. $^1$H NMR (400 MHz, DMSO-$d_6$) δ 8.92 (d, J=4.7 Hz, 1H), 8.28 (d, J=1.7 Hz, 1H), 8.25 (d, J=8.7 Hz 1H), 7.88 (dd, J=1.7, 8.6 Hz, 1H), 7.84 (d, J=4.7 Hz, 1H), 7.64-7.52 (m, 1H), 7.30 (t, J=8.1 Hz, 2H). $^{13}$C NMR (101 MHz, DMSO-$d_6$) δ 162.16 (dd, J=5, 252.3 Hz, 2C), 151.83, 148.07, 141.2, 132.55, 132.16 (t, J=10.1 Hz), 130.06, 125.83, 124.76, 123.5, 122.66, 112.08 (dd, J=5.3, 19 Hz, 2C), 100.4 (t, J=19.7 Hz), 97.62 (t, J=3 Hz), 78.63. HRMS (ESI) calcd for $C_{17}H_9ClF_2N$ [MH+]: 300.0386. Found: 300.0365. Anal. Calcd for $C_{17}H_8ClF_2N$: C, 68.13; H, 2.69; N, 4.67. Found: C, 68.41; H, 2.97; N, 4.42.

6-((2,6-Difluorophenyl)ethynyl)quinolin-4-amine (5cc). Yield 93%; column chromatography using 1:10 methanol-dichloromethane; mp 220-222° C. $^1$H NMR (700 MHz, DMSO-$d_6$) δ 8.54 (s, 1H), 8.35 (br s, 1H), 7.79 (d, J=8.6 Hz, 1H), 7.73 (dd, J=1.7, 8.6 Hz, 1H), 7.61-7.51 (m, 1H), 7.29 (t, J=8 Hz, 2H), 7.27 (s, 2H), 6.62 (d, J=5.3 Hz, 1H). $^{13}$C NMR (176 MHz, DMSO-$d_6$) δ 162.07 (dd, J=5, 251.6 Hz, 2C), 152.28, 150.46, 147.61, 131.44, 131.41 (t, J=10.1 Hz), 128.67, 126.82, 118.06, 116.27, 111.98 (dd, J=5, 18.6 Hz, 2C), 103.1, 100.91 (t, J=19.8 Hz), 99.23 (t, J=3 Hz), 76.01. HRMS (ESI) calcd for $C_{17}H_{11}F_2N_2$ [MH+]: 281.0885. Found: 281.0887. Anal. Calcd for $C_{17}H_{10}F_2N_2$: C, 72.85; H, 3.60; N, 10.00. Found: C, 72.84; H, 3.52; N, 10.06.

7-((2,6-Difluorophenyl)ethynyl)quinolin-4-amine (5dd). Yield 61%; column chromatography using ethyl acetate; mp 219-221° C. $^1$H NMR (700 MHz, DMSO-$d_6$) δ 8.37 (br s, 1H), 8.23 (d, J=8.6 Hz, 1H), 7.94 (s, 1H), 7.6-7.54 (m, 1H), 7.51 (dd, J=1.5, 8.6 Hz, 1H), 7.29 (t, J=8 Hz, 2H), 6.93 (s, 2H), 6.6 (d, J=5.1 Hz, 1H). $^{13}$C NMR (176 MHz, DMSO-$d_6$) δ 162.1 (dd, J=5.0, 251.8 Hz, 2C), 151.45, 151.4, 148.33, 132.32, 131.63 (t, J=10.1 Hz), 125.22, 123.49, 121.57, 118.88, 111.98 (dd, J=3.7, 20.3 Hz, 2C), 103.21, 100.78 (t, J=19.7 Hz), 98.75 (t, J=2.9 Hz), 76.85, HRMS (ESI) calcd for $C_{17}H_{11}F_2N_2$ [MH+]: 281.0885. Found: 281.0885. Anal. Calcd for $C_{17}H_{10}F_2N_2$: C, 72.85; H, 3.60; N, 10.00. Found: C, 72.57; H, 3.73; N, 9.96.

General Procedure for the synthesis of N,N-dimethyl-amino-substituted quinolines by nucleophilic aromatic substitution.

A mixture of 130 mg (0.43 mmol) of an appropriate chloro-substituted quinoline and 2.2 mL (4.3 mmol, 10 eq) of 2M methylamine or dimethylamine in THF was stirred at 130° C. for 2-3 h in a pressure tube. The mixture was poured into water, extracted with dichloromethane, dried over anhydrous magnesium sulfate, concentrated and purified by chromatography as noted for individual compounds.

6-((2,6-Difluorophenyl)ethynyl)-N,N-dimethylquinolin-2-amine (5ee). Yield 67%; preparative layer chromatography using 1:5 ethyl acetate-hexane ($R_f$=0.53) and recrystallization from abs. ethanol; mp 142-144° C. $^1$H NMR (700 MHz, DMSO-$d_6$) δ 8.05 (d, J=9.1 Hz, 1H), 7.98 (d, J=1.9 Hz, 1H), 7.6 (dd, J=2.0, 8.6 Hz, 1H), 7.54 (d, J=8.6 Hz, 1H), 7.53-7.48 (m, 1H), 7.29-7.23 (m, 2H), 7.14 (d, J=9.2 Hz, 1H), 3.19 (s, 6H). $^{13}$C NMR (176 MHz, DMSO-$d_6$) δ 161.97 (dd, J=5.2, 251.1 Hz, 2C), 157.82, 147.85, 136.93, 131.54, 131.42, 130.93 (t, J=10 Hz), 126.25, 121.85, 113.31, 111.88 (dd, J=3.9, 20.2 Hz, 2C), 110.48, 101.25 (t, J=19.8 Hz), 99.78 (t, J=2.9 Hz), 75.07, 37.61 (2C). HRMS (ESI) calcd for $C_{19}H_{15}F_2N_2$ [MH+]: 309.1198. Found: 309.1198, Anal. Calcd for $C_{19}H_{14}F_2N_2$: C, 74.01; H, 4.58; N, 9.09. Found: C, 74.04; H, 4.59; N, 9.09.

6-((2,6-Difluorophenyl)ethynyl)-N,N-dimethylquinolin-4-amine (5ff). Yield 64%; preparative layer chromatography using 1:1 ethyl acetate-hexane ($R_f$=0.41); mp 118-120° C. $^1$H NMR (700 MHz, DMSO-$d_6$) δ 8.62 (d, J=5.2 Hz, 1H), 8.22 (d, J=1.9 Hz, 1H), 7.94 (d, J=8.6 Hz, 1H), 7.76 (dd, J=1.9, 8.6 Hz, 1H), 7.55 (m, 1H), 7.27 (t, J=8 Hz, 2H), 6.91 (d, J=5.2 Hz, 1H), 3.02 (s, 6H). $^{13}$C NMR (176 MHz, DMSO-$d_6$) δ 162.08 (dd, J=5.1, 251.7 Hz, 2C), 156.56, 151.52, 149.18, 131.51 (t, J=10.1 Hz), 130.73, 130.23, 128.42, 121.95, 117.04, 111.95 (dd, J=3.8, 20.2 Hz, 2C), 108.06, 100.84 (t, J=19.7 Hz), 99.05 (t, J=3 Hz), 76.28, 43.54 (2C). HRMS (ESI) calcd for $C_{19}H_{15}F_2N_2$ [MH+]: 309.1198. Found: 309.1201. Anal. Calcd for $C_{19}H_{14}F_2N_2$: C, 74.01; H, 4.58; N, 9.09. Found: C, 73.75; H, 4.66; N, 9.11.

1-((2,6-Difluorophenyl)ethynyl)isoquinoline (5gg). Yield 72%; column chromatography using 1:5 ethyl acetate-hexane; mp 120-122° C. $^1$H NMR (400 MHz, DMSO-$d_6$) δ 8.6 (d, J=5.6 Hz, 1H), 8.45-8.37 (m, 1H), 8.13-8.05 (m, 1H), 7.97 (d, J=5.6 Hz, 1H), 7.92-7.81 (m, 2H), 7.74-7.57 (m, 1H), 7.35 (t, J=8.1 Hz, 2H). $^{13}$C NMR (101 MHz, DMSO-$d_6$) δ 162.44 (dd, J=5, 252.7 Hz, 2C), 143.08, 142.14, 135.38, 132.71 (t, J=10.2 Hz), 131.22, 129.13, 128.6, 127.47, 125.45, 121.74, 112.21 (dd, J=5.4, 18.3 Hz, 2C), 100.04 (t, J=19.7 Hz), 96.00 (t, J=3.1 Hz), 80. HRMS (ESI) calcd for $C_{17}H_{10}F_2N$ [MH+]: 266.0776. Found: 266.0758. Anal. Calcd for $C_{17}H_9F_2N$: C, 76.98; H, 3.42; N, 5.28. Found: C, 76.92; H, 3.50; N, 5.20.

4-((2,6-Difluorophenyl)ethynyl)isoquinoline (5hh). Yield 73%; column chromatography using 1:5 ethyl acetate-hexane; mp 102-104° C. $^1$H NMR (400 MHz, DMSO-$d_6$) δ 9.41 (s, 1H), 8.79 (s, 1H), 8.25 (t, J=9.1 Hz, 2H), 7.99 (t, J=7.6 Hz, 1H), 7.82 (t, J=7.6 Hz, 1H), 7.68-7.53 (m, 1H), 7.32 (t, J=8.1 Hz, 2H). $^{13}$C NMR (101 MHz, DMSO-$d_6$) δ 162.04 (dd, J=5, 252.1 Hz, 2C), 153.34, 146.2, 134.33, 132.32, 132.06 (t, J=10.2 Hz), 128.63, 128.57, 127.34, 123.75, 113.84, 112.09 (dd, J=4.9, 18.6 Hz, 2C), 100.58 (t, J=19.6 Hz), 94.01 (t, J=3 Hz), 83.24. HRMS (ESI) calcd for $C_{17}H_{10}F_2N$ [MH+]: 266.0776. Found: 266.0758. Anal. Calcd for $C_{17}H_9F_2N$: C, 76.98; H, 3.42; N, 5.28. Found: C, 76.68; H, 3.49; N, 5.10.

5-((2,6-Difluorophenyl)ethynyl)isoquinoline (5ii), Yield 85%; column chromatography using 1:1 ethyl acetate-hexane; mp 115-117° C. $^1$H NMR (400 MHz, DMSO-$d_6$) δ 9.44 (s, 1H), 8.7 (d, J=5.8 Hz, 1H), 8.27 (d, J=8.3 Hz, 1H), 8.11 (dd, J=1.1, 7.2 Hz, 1H), 8.08 (d, J=5.9 Hz, 1.11), 7.81-7.72 (m, 1H), 7.66-7.55 (m, 1H), 7.33 (t, J=8.1 Hz, 2H). $^{13}$C NMR (101 MHz, DMSO-$d_6$) δ 162.06 (dd, J=5.1, 252 Hz, 2C), 153.14, 144.54, 134.88, 134.71, 131.97 (t, J=10.1 Hz), 129.62, 127.91, 127.36, 117.86, 117.53, 112.1 (dd, J=5.3, 19 Hz, 2C), 100.63 (t, J=19.6 Hz), 95.41 (t, J=3 Hz), 81.86. HRMS (ESI) calcd for $C_{17}H_{10}F_2N$ [MH+]: 266.0776. Found: 266.0756. Anal. Calcd for $C_{17}H_9F_2N$: C, 76.98; H, 3.42; N, 5.28. Found: C, 76.75; H, 3.47; N, 5.23.

6-((2,6-difluorophenyl)ethynyl)isoquinoline (5jj). Yield 75%, column chromatographing using 1:1 ethyl acetate-hexane; mp 97-99° C. $^1$H NMR (400 MHz, DMSO-$d_6$) δ 9.38 (s, 1H), 8.58 (d, J=6.1 Hz, 1H), 8.3 (s, 1H), 8.2 (d, J=8.5 Hz, 1H), 7.9 (d, J=5.7 Hz, 1H), 7.79 (dd, J=1.6, 8.5 Hz, 1H), 7.68-7.5 (m, 1H), 7.3 (t, J=8.1 Hz, 2H). $^{13}$C NMR (101 MHz, DMSO-$d_6$) δ 162.18 (dd, J=5, 252.1 Hz, 2C), 152.35, 143.91, 134.84, 132.1 (t, J=10.2 Hz), 130.25, 129.29, 128.44, 123.12, 120.19, 112.11 (dd, J=5.0, 19 Hz, 2C), 100.37 (t, J=19.7 Hz), 98.29 (t, J=3.2 Hz), 78.06. HRMS (ESI) calcd for $C_{17}H_{10}F_2N$ [MH+]: 266.0776. Found: 266.0757. Anal. Calcd for $C_{17}H_9F_2N$: C, 76.98; H, 3.42; N, 5.28. Found: C, 77.16; H, 3.39; N, 5.21.

1-Chloro-4-((2,6-difluorophenyl)ethynyl)isoquinoline (5kk). Yield 48%; preparative layer chromatography using 1:5 ethyl acetate-hexane ($R_f$=0.62) and recrystallization from abs. ethanol; mp 145-146° C. $^1$H NMR (700 MHz, DMSO-$d_6$) δ 8.63 (s, 1H), 8.39 (d, J=8.2 Hz, 1H), 8.3 (d, J=8.3 Hz, 1H), 8.1 (ddd, J=1.2, 6.9, 8.2 Hz, 1H), 7.95 (ddd, J=1.1, 6.9, 8.3 Hz, 1H), 7.66-7.58 (m, 1H), 7.33 (t, J=8.1 Hz, 2H). $^{13}$C NMR (176 MHz, DMSO-$d_6$) δ 162.06 (dd, J=4.9, 252.5 Hz, 2C), 151.11, 144.73, 136.29, 133.31, 132.36 (t, J=10.1 Hz), 130.35, 126.5, 125.37, 124.82, 114.66, 112.13 (dd, J=3.7, 20.1 Hz, 2C). 100.31 (t, J=19.7 Hz), 93 (t, J=3.0 Hz), 84.26. HRMS (ESI) calcd for $C_{17}H_9ClF_2N$ [MH+]: 300.0386. Found: 300.0388. Anal. Calcd for $C_{17}H_8ClF_2N$: C, 68.13; H, 2.69; N, 4.67. Found: C. 68.06; H, 2.78; N, 4.61.

1-((2,6-Difluorophenyl)ethynyl)-7-fluoroisoquinoline (5ll). Yield 56%; column chromatography using 1:200 methanol-dichloromethane; mp 177-178° C. $^1$H NMR (400 MHz, DMSO-$d_6$) δ 8.61 (d, J=5.5 Hz, 1H), 8.23 (dd, J=5.5, 9.1 Hz, 1H), 8.07-7.96 (m, 2H), 7.83 (td, J=2.6, 8.9 Hz, 1H), 7.71-7.57 (m, 1H), 7.35 (t, J=8.2 Hz, 2H). $^{13}$C NMR (101 MHz, DMSO-$d_6$) δ 162.43 (dd, J=5, 252.8 Hz, 2C), 161.17 (d, J=249.3 Hz), 142.77 (d, J=2.4 Hz), 141.58 (d, J=6 Hz), 132.93, 132.79 (d, J=8.6 Hz), 131.15 (d, J=8.9 Hz), 129.49 (d, J=8.8 Hz), 121.79 (d, J=25.6 Hz), 121.56 (d, J=1.6 Hz), 112.23 (dd, J=5, 18.7 Hz, 2C), 108.72 (d, J=22.2 Hz), 99.91 (t, J=19.7 Hz), 95.49 (t, J=2.7 Hz), 80.54. HRMS (ESI) calcd for $C_{17}H_9F_3N$ [MH+]: 284.0682. Found: 284.0662. Anal. Calcd for $C_{17}H_8F_3N$: C, 72.09; H, 2.85; N, 4.95. Found: C, 71.98; H, 2.69; N, 4.91.

4-((2,6-Difluorophenyl)ethynyl)isoquinolin-1-amine (5mm). Yield 71%; column chromatography using 1:10 methanol-dichloromethane and recrystallization from methanol; mp 200-201° C. $^1$H NMR (400 MHz, DMSO-$d_6$) δ 8.31 (d, J=8.3 Hz, 1H), 8.17 (s, 1H), 8.04 (d, J=8.2 Hz, 1H), 7.82 (t, J=7.6 Hz, 1H), 7.59 (t, J=7.6 Hz, 1H), 7.55-7.43 (m, 3H), 7.26 (t, J=7.9 Hz, 2H). $^{13}$C NMR (101 MHz, DMSO-$d_6$) δ 162.04 (dd, J=5.4, 250.5 Hz, 2C), 158.49, 147.85, 136.25, 131.71, 130.77 (t, J=10 Hz), 126.86, 125, 124.33, 116.64, 111.85 (dd, J=5.4, 18.3 Hz, 2C), 102.27, 102.23 (t, J=19.9 Hz), 97.26 (t, J=2.9 Hz), 80.27. HRMS (ESI) calcd for $C_{17}H_{11}F_2N_2$ [MH+]: 281.0885. Found: 281.0866. Anal. Calcd for $C_{17}H_{10}F_2N_2$: C, 72.85; H, 3.60; N, 10.00. Found: C, 73.13; H, 3.69; N, 9.93.

4-((2,6-difluorophenyl)ethynyl)-N,N-dimethylisoquinolin-1-amine (5nn). Yield 75%; preparative layer chromatography using 1:5 ethyl acetate-hexane ($R_f$=0.47); mp 122-124° C. $^1$H NMR (700 MHz, DMSO-$d_6$) δ 8.31 (s, 1H), 8.23-8.16 (m, 1H), 8.13 (dd, J=1.2, 8.3 Hz, 1H), 7.84 (ddd, J=1.2, 6.9, 8.2 Hz, 1H), 7.62 (ddd, J=1.3, 6.8, 8.3 Hz, 1H), 7.56-7.48 (m, 1H), 7.28 (t, J=7.9 Hz, 2H), 3.19 (s, 6H). $^{13}$C NMR (176 MHz, DMSO-$d_6$) δ 161.72 (dd, J=5.3, 250.9 Hz, 2C), 160.63, 145.03, 137.01, 130.96, 130.82 (t, J=10.1 Hz), 126.80, 126.2, 124.21, 118.3, 111.91 (dd, J=3.8, 20.1 Hz, 2C), 105.07, 101.45 (t, J=19.8 Hz), 95.96 (t, J=2.9 Hz), 81.00, 42.45 (2C). HRMS (ESI) calcd for $C_{19}H_{15}F_2N_2$ [MH+]: 309.1198. Found: 309.1200. Anal. Calcd for $C_{19}H_{14}F_2N_2$: C, 74.01; H, 4.58; N, 9.09. Found: C, 73.75; H, 4.60; N, 9.00.

4-((2,6-Difluorophenyl)ethynyl)-N-methylisoquinolin-1-amine (5oo). Yield 60%, $R_f$=0.48 (1:2 ethyl acetate-hexane), mp 118-120° C. $^1$H NMR (400 MHz, DMSO-$d_6$) δ 8.28 (d, J=8.6 Hz, 1H), 8.25 (s, 1H), 8.08 (d, J=4.5 Hz, 1H), 8.05 (d, J=9.1 Hz, 1H), 7.81 (t, J=7.5 Hz, 1H), 7.61 (t, J=7.5 Hz, 1H), 7.55-7.44 (m, 1H), 7.26 (t, J=7.9 Hz, 2H), 3.03 (d, J=4.5 Hz, 3H). $^{13}$C NMR (101 MHz, DMSO-$d_6$) δ 161.61 (dd, J=5.4, 250.4 Hz, 2C), 156.29, 147.12, 135.26, 130.99, 130.33 (t, J=10.1 Hz), 126.6, 124.05, 123.44, 117.01, 112.01 (dd, J=3.8, 20.1 Hz, 2C), 101.78 (t, J=19.9 Hz), 101.45, 96.88 (t, J=2.9 Hz), 79.90, 28.29. HRMS (ESI) calcd for $C_{18}H_{13}F_2N_2$ [MH+]: 295.1041. Found: 295.1035. Anal. Calcd for $C_{18}H_{12}F_2H_2$: C, 73.46; H, 4.11; N, 9.52. Found: C, 73.49; H, 4.23, N, 9.61.

4-((2,6-Difluorophenyl)ethynyl)-1-(4-methylpiperazin-1-yl)isoquinoline (5pp). Yield 79%, $R_f$=0.42 (1:10 methanol-dichloromethane), mp 70-72° C. $^1$H NMR (400 MHz, DMSO-$d_6$) δ 8.38 (s, 1H), 8.16 (d, J=8.1 Hz, 1H), 8.11 (d, J=8.4 Hz, 1H), 7.88 (ddd, J=1.2, 6.9, 8.2 Hz, 1H), 7.68 (ddd, J=1.3, 6.9, 8.3 Hz, 1H), 7.61-7.5 (m, 1H), 7.29 (t, J=8 Hz, 2H), 3.47 (t, J=5 Hz, 4H), 2.57 (t, J=4.7 Hz, 4H), 2.27 (s, 3H). $^{13}$C NMR (101 MHz, DMSO-$d_6$) δ 161.82 (dd, J=5.3, 251.1 Hz, 2C), 160.77, 144.84, 136.70, 131.31, 131.15 (t, J=9.2 Hz), 127.19, 126.14, 124.54, 119.27, 112.12 (dd, J=3.7, 20.1 Hz, 2C). 107.32, 101.20 (t, J=19.7 Hz), 95.34 (t, J=3 Hz), 81.52, 54.56 (2C), 50.65 (2C), 45.78. HRMS (ESI) calcd for $C_{22}H_{20}F_2N_3$ [MH+]: 364.1620. Found: 364.1614. Anal. Calcd for $C_{22}H_{19}F_2N_3$: C, 72.71; H, 5.27; N, 11.56. Found: C, 72.91; H, 5.12, N, 11.67.

8-((2,6-Difluorophenyl)ethynyl)-N,N-dimethyl-1,6-naphthyridin-5-amine (5qq). Yield 76%, $R_f$=0.29 (1:2 ethyl acetate-hexane), mp 149-150° C. $^1$H NMR (400 MHz, DMSO-$d_6$) δ 9.04 (dd, J=1.7, 4.2 Hz, 1H), 8.59 (dd, J=1.7, 8.5 Hz, 1H), 8.45 (s, 1H), 7.57 (dd, J=4.2, 8.5 Hz, 1H), 7.53-7.46 (m, 1H), 7.25 (t, J=8 Hz, 2H), 3.25 (s, 6H). $^{13}$C NMR (101 MHz, DMSO-$d_6$) δ 161.9 (dd, J=5.3, 250.9 Hz, 2C), 160.35, 153.88, 152.18, 148.92, 135.3, 130.67 (t, J=10.1 Hz), 120.82, 113.48, 111.84 (dd, J=3.8, 20.1 Hz, 2C), 106.58, 101.86 (t, J=19.8 Hz), 96.37 (t, J=3.0 Hz), 79.73, 42.31 (2C). HRMS (ESI) calcd for $C_{18}H_{14}F_2N_3$ [MH+]: 310.1150. Found: 310.1147. Anal. Calcd for $C_{18}H_{13}F_2N_3$: C, 69.89; H, 4.24; N, 13.58. Found: C, 70.01; H, 4.44, N, 13.53.

7-((2,6-Difluorophenyl)ethynyl)quinazoline (5rr). Yield 68%; recrystallized from acetonitrile; mp 166-168° C. $^1$H NMR (400 MHz, DMSO-$d_6$) δ 9.68 (s, 1H), 9.37 (s, 1H), 8.25 (d, J=8.4 Hz, 1H), 8.2 (s, 1H), 7.89 (dd, J=1.6, 8.4 Hz, 1H), 7.69-7.53 (m, 1H), 7.31 (t, J=8.1 Hz, 2H). $^{13}$C NMR (101 MHz, DMSO-$d_6$) δ 162.19 (dd, J=4.9, 252.6 Hz, 2C), 160.85, 156.02, 148.92, 132.46 (t, J=10.2 Hz), 130.75, 130.11, 128.79, 127.1, 124.50, 112.14 (dd, J=5, 18.6 Hz, 2C), 100.21 (t, J=19.7 Hz), 97.51 (t, J=3 Hz), 79.73. HRMS (ESI) calcd for $C_{15}H_9F_2N_2$ [MH+]: 267.0728. Found: 267.0710. Anal. Calcd for $C_{16}H_8F_2N_2$: C, 72.18; H, 3.03; N, 10.52. Found: C, 71.97; H, 3.22; N, 10.29.

3,5-Difluoro-4-(phenylethynyl)pyridine (7a). Yield 88%; preparative layer chromatography using 1:20 ethyl acetate-hexane ($R_f$=0.48); mp 52-54° C. $^1$H NMR (400 MHz, DMSO-$d_6$) δ 8.67 (s, 2H), 7.69-7.62 (m, 2H), 7.58-7.47 (m, 3H). $^{13}$C NMR (101 MHz, DMSO-$d_6$) δ 157.60 (d, J=264.1 Hz, 2C), 134.52 (dd, J=21.8, 4.6 Hz, 2C), 131.87 (2C), 130.58, 129.09 (2C), 120.20, 108.59 (t, J=16.5 Hz), 103.10 (t, J=2.9 Hz), 73.82. HRMS (ESI) calcd for $C_{13}H_8F_2N$ [MH+]: 216.0619. Found: 216.0619. Anal. Calcd for $C_{13}H_7F_2N$: C, 72.56; H, 3.28; N, 6.51. Found: C, 72.78; H, 3.38, N, 6.58.

4-((3,5-Difluoropyridin-4-yl)ethynyl)aniline (7b). Yield 69%; preparative layer chromatography using 1:5 ethyl acetate-hexane ($R_f$=0.3); mp 156-158° C., $^1$H NMR (400 MHz, DMSO-$d_6$) δ 8.58 (s, 2H), 7.28 (d, J=8.4 Hz, 2H), 6.59 (d, J=8.3 Hz, 2H), 5.91 (s, 2H, $NH_2$). $^{13}$C NMR (101 MHz, DMSO-$d_6$) δ 157.31 (d, J=262.2 Hz, 2C), 151.19, 134.17 (dd, J=21.5, 4.8 Hz, 2C), 133.48 (2C), 113.62 (2C), 109.81 (t, J=16.7 Hz), 106.67 (t, J=2.9 Hz), 105.47, 71.86. HRMS (ESI) calcd for $C_{13}H_9F_2N_2$ [MH+]: 231.0728. Found: 231.0730. Anal. Calcd for $C_{13}H_8F_2N_2$: C, 67.82; H, 3.50; N, 12.17. Found: C, 67.64; H, 3.69, N, 12.10.

4-((3,5-Difluoropyridin-4-yl)ethynyl)-N-methylaniline (7c). Yield 54%; preparative layer chromatography using 1:5 ethyl acetate-hexane ($R_f$=0.26); mp 149-151° C. $^1$H NMR (400 MHz, DMSO-$d_6$) δ 8.60 (s, 2H), 7.35 (d, J=8.6 Hz, 2H), 6.58 (d, J=8.6 Hz, 2H), 6.49 (q, J=5.0 Hz, 1H), 2.72 (d, J=5.0 Hz, 3H). $^{13}$C NMR (101 MHz, DMSO-$d_6$) δ 157.30 (d, J=262.2 Hz, 2C), 151.50, 134.17 (dd, J=21.6, 4.9 Hz, 2C), 133.41 (2C), 111.54 (2C), 109.80 (t, J=16.6 Hz), 106.66 (t, J=2.8 Hz), 105.34, 72.10, 29.16. HRMS (ESI) calcd for $C_{14}H_{11}F_2N_2$ [MH+]: 245.0885. Found: 245.0885. Anal. Calcd for $C_{14}H_{10}F_2N_2$: C, 68.85; H, 4.13; N, 11.47, Found: C, 68.64; H, 4.40, N, 11.27.

4-((3,5-Difluoropyridin-4-yl)ethynyl)-N,N-dimethylaniline (7d). Yield 78%; preparative layer chromatography using 1:5 ethyl acetate-hexane ($R_f$=0.47); mp 39-140° C. $^1$H NMR (400 MHz, DMSO-$d_6$) δ 8.60 (s, 2H), 7.43 (d, J=8.5 Hz, 2H), 6.74 (d, J=8.6 Hz, 2H), 2.99 (s, 6H). $^{13}$C NMR (101 MHz, DMSO-$d_6$) δ 157.32 (d, J=262.4 Hz, 2C), 151.14, 134.21 (dd, J=21.6, 4.8 Hz, 2C), 133.21 (2C), 111.80 (2C), 109.67 (t, J=16.7 Hz), 106.17 (t, J=2.9 Hz), 105.72, 72.48, 39.59 (2C). HRMS (ESI) calcd for $C_{15}H_{13}F_2N_2$ [MH+]: 259.1041. Found: 259.1041. Anal. Calcd for $C_{15}H_{12}F_2N_2$: C, 69.76; H, 4.68; N, 10.85. Found: C, 69.50; H, 4.78, N, 10.78.

Cell proliferation assay. LS174T cells were grown in RPMI medium (Mediatech) supplemented with 5% fetal bovine serum and 1% penicillin/streptomycin. For cell proliferation assays, $3 \times 10^4$ cells/well growing in 12-well plates were treated with DMSO or inhibitors. The cell numbers and viability were analyzed by Vi-Cell Cell Viability Analyzer after 4 days. The $IC_{50}$ values were calculated with GraphPad Prim 5.

Western blotting. Western blotting was performed as described previously. The following antibodies were used: anti-c-myc (Epitomics, 1472-1), anti-p21$^{Wif1/Cip1}$ (Cell Signaling, 2947), anti-β-tubulin (DSHB, E7).

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A pharmaceutical composition comprising a compound according to the following formula (I):

or a pharmaceutically acceptable salt thereof, and a pharmaceutically acceptable carrier;
wherein each of $X_1$ through $X_5$ independently represents H, a lower alkyl, alkoxy, halo, and/or $NR_1R_2$;
wherein n is either 1 or 0 and when n is 1, each of $Y_1$ through $Y_4$ independently represents H, a lower alkyl or alkoxy, or $NR_1R_2$;
wherein Heterocycle represents a pyridine;
wherein $Y_5$ includes two or more halogens which can be the same or different; and
wherein each of $R_1$ and $R_2$ independently represent H or a lower alkyl.

2. The pharmaceutical composition of claim 1, wherein $Y_5$ includes at least two fluoro groups.

3. The pharmaceutical composition of claim 1, wherein n is 0 and at least one of $X_1$ through $X_5$ is $NR_1R_2$.

4. The pharmaceutical composition of claim 3, wherein $X_3$ represents $NR_1R_2$.

5. The pharmaceutical composition of claim 3, wherein both of $R_1$ and $R_2$ are methyl.

6. A method of treating cancer, the method comprising administering to a patient in need of such treatment an effective amount of a compound according to claim 1.

7. A pharmaceutical composition comprising a compound according to the following formula (I):

(I)

or a pharmaceutically acceptable salt thereof, and a pharmaceutically acceptable carrier;
wherein each of $X_1$ through $X_5$ independently represents H, a lower alkyl, alkoxy, halo, and/or $NR_1R_2$; n is either 1 or 0 and when n is 1, each of $Y_1$ through $Y_4$ independently represents H, a lower alkyl or alkoxy, or $NR_1R_2$; Heterocycle represents a heterocycle ring selected among oxopiperidine, morpholine, piperazine, N-methylpiperazine, N-pyrrole, 2,5-dimethyl-N-pyrrole, quinoline, isoquinoline, indole, indazole, and naphthyridine; and $Y_5$ represents one or more $NR_1R_2$, or one or more halogens which can be the same or different, wherein each of $R_1$ and $R_2$ independently represent H, or a lower alkyl.

8. The pharmaceutical composition of claim 7, wherein at least two of $X_1$ through $X_5$ is are halo groups.

9. The pharmaceutical composition of claim 7, wherein $X_1$ through $X_5$ is either:

(i) a fluoro and chloro, (ii) both fluoro, (iii) both chloro groups.

10. A method of treating cancer, the method comprising administering to a patient in need of such treatment an effective amount of a compound according to claim 7.

11. The method of claim 10, wherein at least two of $X_1$ through $X_5$ are halo groups.

12. The method of claim 11, wherein $X_1$ through $X_5$ is either (i) a fluoro and chloro, (ii) both fluoro, or (iii) both chloro groups.

13. The method of claim 10, wherein both $R_1$ and $R_2$ are lower alkyl groups.

14. The method of claim 13, wherein either $X_1$ or $X_5$ or both $X_1$ and $X_5$ are halo groups and $X_2$ through $X_4$ are H or a lower alkyl.

15. The method of claim 10, wherein $X_1$ and/or $X_5$ are halo groups, $X_2$ through $X_4$ are H or a lower alkyl, $Y_3$ is $NR_1R_2$, and $Y_1$, $Y_2$, $Y_4$, and $Y_5$ independently represent H or a lower alkyl.

16. The method of claim 10, wherein $X_1$ and/or $X_5$ are fluoro and/or chloro and at least one of $R_1$ or $R_2$ is a lower alkyl.

17. The method of claim 10, wherein n is 0 and the heterocycle ring is a lower alkyl substituted or unsubstituted N-pyrrole.

18. The method of claim 10, wherein n is 0 and the heterocycle ring is a lower alkyl substituted or unsubstituted isoquinoline.

19. The method of claim 10, wherein the cancer treated is selected from the group consisting of colorectal cancer, leukemias, breast cancer, ovarian cancer, lung cancer, prostate cancer, and liver cancer.

20. The method of claim 10, wherein the cancer treated is colorectal cancer.

* * * * *